United States Patent
Tuchman et al.

(10) Patent No.: US 7,206,701 B2
(45) Date of Patent: Apr. 17, 2007

(54) SYSTEMS AND METHODS FOR AUTOMATED QUANTITATIVE ANALYSIS OF DIGITIZED SPECTRA

(75) Inventors: Donald P. Tuchman, Pittsburgh, PA (US); Donald H. Lemmon, Verona, PA (US); Brian C. Smith, Shrewsbury, MA (US)

(73) Assignee: United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 10/499,443

(22) PCT Filed: Dec. 17, 2002

(86) PCT No.: PCT/US02/40315

§ 371 (c)(1),
(2), (4) Date: Jun. 18, 2004

(87) PCT Pub. No.: WO03/056300

PCT Pub. Date: Jul. 10, 2003

(65) Prior Publication Data

US 2005/0019946 A1    Jan. 27, 2005

Related U.S. Application Data

(60) Provisional application No. 60/342,624, filed on Dec. 21, 2001.

(51) Int. Cl.
*G01N 21/35* (2006.01)

(52) U.S. Cl. .............. 702/24; 702/22; 702/23; 702/30; 702/32; 250/339.08

(58) Field of Classification Search ........... 702/22–24, 702/27, 28, 30–32, 19, 75–78, 85, 189, 191; 250/339.06–339.09, 339.11, 339.12, 339.13, 250/341.3, 341.8, 338.1, 338.5, 252.1; 356/302, 356/303, 432, 436, 437, 428; 345/440
See application file for complete search history.

(56) References Cited

U.S. PATENT DOCUMENTS

| | | | |
|---|---|---|---|
| 5,459,677 A | 10/1995 | Kowalski et al. | 703/2 |
| 5,545,895 A | 8/1996 | Wright et al. | 250/282 |
| 5,579,462 A * | 11/1996 | Barber et al. | 345/440 |

(Continued)

OTHER PUBLICATIONS

"Smart Purge System," Thermo Nicolet, 1 page, Copyright 2001.*

(Continued)

*Primary Examiner*—Hal Wachsman
(74) *Attorney, Agent, or Firm*—Klarquist Sparkman, LLP

(57) ABSTRACT

A variety of methods and systems related to automated quantitative analyses via digital spectroscopy techniques can be used to determine the quantity of one or more analytes in a sample. A parameter file can be used to control automated analysis. Suspect conditions related to parameters can be identified and-appropriate advisories provided. Suspect conditions related to analysis can be identified and appropriate warnings provided. Various algorithmic techniques are supported and can be selected by a user by modifying parameters via a parameter-editing user interface presented by software.

46 Claims, 22 Drawing Sheets

U.S. PATENT DOCUMENTS

| | | | | |
|---|---|---|---|---|
| 5,633,997 | A | * | 5/1997 | Barber et al. ............... 345/440 |
| 5,760,785 | A | | 6/1998 | Barber et al. ............... 345/440 |
| 5,807,750 | A | | 9/1998 | Baum et al. ................ 436/164 |
| 5,838,008 | A | | 11/1998 | Esler et al. ............ 250/339.08 |
| 5,867,265 | A | | 2/1999 | Thomas ...................... 356/328 |
| 5,885,531 | A | | 3/1999 | Heffelfinger et al. .... 422/82.05 |
| 6,108,082 | A | | 8/2000 | Pettipiece et al. .......... 356/301 |
| 6,284,196 | B1 | | 9/2001 | Casal et al. ................... 422/62 |
| 6,395,538 | B1 | | 5/2002 | Naughton et al. ....... 435/288.7 |
| 6,452,179 | B1 | * | 9/2002 | Coates et al. .......... 250/339.09 |

OTHER PUBLICATIONS

"AutoQuant Quantitative Analysis Software", 1 page, Aug. 7, 2001.*
"IR Search/Sadtler for GRAMS/386™," Galactic Industries Corporation, pp. 20-23, 36-39 and 52-55, Copyright 1991-1994, no month.
"Add-on Application, QuantBasic™ for GRAMS/386®," Galactic Industries Corporation, pp. i-41, Copyright 1991-1995, no month.
"GRAMS/32® Version 5 User's Guide," Galactic Industries Corporation, pp. 126-227, 298-301 and 416-421, Copyright 1991-1997.
"Add-on Application PLSplus/IQ™ for GRAMS/32®," Galactic Industries Corporation, pp. i-199, Copyright 1991-1997, no month.
"Spectral ID™ User's Guide," Galactic Industries Corporation, pp. 26-31 and 46-47, Copyright 1991-1998, no month.
"Spectral ID® User's Guide," Thermo Galactic, pp. 10-13, 24-29, 60-61 and 82-85, Copyright 1991-2001.
"Spectroscopy Software Solutions: Product Catalog," Thermo Electron Corporation, 18 pages, Nov. 2002.
Thermo Electron Corporation Product Price List, 2 pages, Mar. 2003.
"Manufacturer Directory," Thermo Galactic, 1 page, at least as early as Jul. 16, 2004.
"GRAMS AI Active Apps—QuickQuant," http://www.galactic.com/products/GRAMS_32/quickquant.htm, 3 pages, website visited on Jun. 11, 2002.
"My Instrument Compliant Software Vendors," http://www.myinstrument.com/vendors/htm, 3 pages, website visited on Sep. 5, 2002.
"GRAMS/AI™ User's Guide," Thermo Galactic, pp. 6-9, 50-54, 112-119 and 167-379, Copyright 1991-2001, no month.
"Optical Solutions: OS-MLR Multiple Linear Regression V2.00," Optical Solutions, Inc., 30 pages, Copyright 1998, no month.
"Omni—Home," http://www.omniinstruments.com/, Optical Scientific Instruments, Inc., 2 pages, Feb. 16, 2002.
"Omni—Products," http://www.omniinstruments.com/products.html, Optical Scientific Instruments, Inc., 2 pages, Feb. 16, 2002.
"Omni—WRFWIN for WDS," http://www.omniinstruments.com/xrfwinwds.html, Optical Scientific Instruments, Inc., 13 pages, Mar. 2, 2002.
"TASI—X-Ray Analysis," http://www.tasitechnical.com/xray.html, TASI Technical Software Inc., 1 page, May 27, 2002.
"AutoQuant™: Software for Gas Phase Infrared Spectral Analysis," brochure, MIDAC Corporation, screen shot shows Jan. 13, 1998.
"Analect® ChemEye: FTIR Analyzer," brochure, Hamilton Sundstrand, 4 pages, Jul. 2001.
"EZ OMNIC® FT-IR Software," brochure, Thermo Nicolet, 4 pages, Aug. 2001.
"OMNIC Software," brochure, Thermo Nicolet, 4 pages, Sep. 2002.
"OMNIC® Macros\Basic™," brochure, Thermo Nicolet, 2 pages, Apr. 2001.
"TQ Analyst—Professional Edition," Thermo Electron Corporation, 4 pages, Dec. 2002.
"OPtics User Software," Bruker Optics Inc., 14 pages, 2002, no month.
"IR Prestige-21," brochure, Shimadzu Corporation, 3 pages, screen shot shows Mar. 14, 2002.
"Fourier Transform Infrared Spectrophotometer: FTIR-8400S," Shimadzu Corporation, 3 pages, screen shot shows Mar. 14, 2002.

"EZ-Pick™," SensIR Technologies, 1 page, Copyright 1999, no month.
"Spectroscopy Product Showcase," Scientific Computing & Instrumentation™, pp. 52, 53 and 55, May 2002.
"Spectroscopy Software Resource Guide," Scientific Computing & Instrumentation™, p. 39, Aug. 2002.
"The Road to Compliance—Are You There Yet?" The Galactic Enquirer, 8 pages, Mar. 2002.
"RazorTools6," www.spectrumsquare.com/razortools6.htm, 2 pages, May 27, 2000.
"About Galactic" Galactic Industries Corporation, http://www.galactic.com/about/, 2 pages, website visited on Dec. 6, 2000.
"About Us" Optical Solutions, Inc., http://www.optical-solutions.com/about.html, 2 pages, website visited on Dec. 4, 2000.
"Array Basic Information" Galactic Industries Corporation, http://www.galactic.com/Programming/abinfo.htm, 2 pages, website visited on Dec. 4, 2000.
"Array Basic Programming for Galactic Software" Galactic Industries Corporation, http://www.galactic.com/Programming/, 5 pages, website visited on Dec. 4, 2000.
"Array Basic Programming for Galactic Software" Thermo Galactic, http://www.galactic.com/Programming/Default.asp, 5 pages, website visited on Dec. 7, 2001.
"Auto Subtraction Array Basic Routine" Galactic Industries Corporation, http://www.galactic.com/Programming/auto_subtraction.htm, 1 page, website visited on Dec. 6, 2000.
"Development of a Simple, Rapid Analysis Method for Respirable Dust" Department of the Interior Bureau of Mines, Operating Instructions, 37 pages, Mar. 7, 1974.
"Development of a Simple, Rapid Analysis Method for Respirable Dust" Department of the Interior Bureau of Mines, The Silgard Manual, 81 pages, Mar. 20, 1974.
"Find Peak Array Basic Routine" Galactic Industries Corporation, http://www.galactic.com/Programming/find_peak.htm, 1 page, website visited on Dec. 6, 2000.
"Galactic Algorithms" Galactic Industries Corporation, http://www.galactic.com/Algorithms/, 3 pages, website visited on Dec. 4, 2000.
"Galactic Industries Corporation: Spectroscopy Software Solutions" Galactic Industries Corporation, http://www.galactic.com/, 2 pages, website visited on Dec. 4, 2000.
"Galactic Products" Galactic Industries Corporation, http://www.galactic.com/products/, 2 pages, website visited on Dec. 4, 2000.
"GRAMS/32 Version 5.2" Galactic Products, Galactic Industries Corporation, http://www.galactic.com/products/GRAMS_32/main.htm, 2 pages, website visited on Dec. 4, 2000.
"GRAMS/32 Third Party Applications" Galactic Products, Galactic Industries Corporation, http://www.galactic.com/products/third_party.htm, 2 pages, website visited on Dec. 4, 2000.
"Health & Safety Laboratory: MDHS Titles" Methods for the Determination of Hazardous Substances, http://www.hsl.gov.uk/services/mdhs_list.htm, 10 pages, website visited on Dec. 19, 2001.
"Infrared Analysis, Inc.: The Company and Its Products" Infrared Analysis, Inc., 3 pages, http://www.infraredanalysisinc.com/nrpd1.htm, website visited on Oct. 22, 2001.
"Infrared Determination of Quartz in Respirable Coal Mine Dust" Department of Labor Mine Safety and Health Administration, Pittsburgh Safety and Health Technology Center, 14 pages, May 25, 1999.
"NIOSH 7500 Air Sampling Information for Quartz (Silica, Crystalline (respirable)) by KRD" SKC Inc., http://www.skcinc.com/NIOSH1/FILE2109.asp, website visited on Mar. 22, 2001.
"OMNI—XRFWIN 3.1" Omni Scientific Instruments, Inc., http://www.omniinstruments.com/xrfwin.html, 6 pages, archived on Mar. 27, 2002.
"OSHA Directives—CPL 2-2.7—Crystalline Silica" Occupational Safety & Health Administration, U.S. Department of Labor, 53 pages, http://www.osha-slc.gov/OshDoc/Directive_data/CPL_2-2_7.html, website visited on Mar. 22, 2001.
"OS-MLR—Multiple Linear Regression for GRAMS" Optical Solutions, Inc., Datasheet, Mar. 22, 2001.
"Peak Characterizations, X Coordinate of True Peak Max" Galactic Industries Corporation, http://www.galactic.com/Algorithms/pc_xcoord.htm, 1 page, website visited on Dec. 6, 2000.

"Peak Picking" Thermo Galactic, http://www.galatic.com/Algorithms/peak_picking.htm, 5 pages, website visited on Dec. 7, 2001.

"Qualitative Analysis with XRFWIN" Tasker Applications, 3 pages, http://www.tasitechnical.com/tapp/qual.html, website visited on Nov. 1, 2001.

"Quantitative Analysis with XRFWIN" Tasker Applications, 3 pages, http://www.tasitechnical.com/tapp/quant.html, website visited on Nov. 1, 2001.

"Quartz Analytical Method (P-7): Infrared Determination of Quartz in Respirable Coal Mine Dust" Occupational Safety & Health Administration, U.S. Department of Labor, http://www.osha-slc.gov/SLTC/silicacrystalline/p7/p7.html, 12 pages, website visited on Oct. 22, 2001.

"Quartz in Respirable Airborne Dusts: Laboratory Method Using Infra-red Spectroscopy (Direct Method)" Occupational Medicine and Hygiene Laboratory, MDHS 37, Methods for Determination of Hazardous Substances, 8 pages, (Revised) Nov. 1987.

"References: Galactic Algorithms" Galactic Industries Corporation, http://www.galactic.com/Algorithms/references.htm, 4 pages, website visited on Dec. 6, 2000.

"Silica, Amorphous" NIOSH Manual of Analytical Methods (NMAM), Fourth Edition, Method 7501, Issue 2, http://www.cdc.gov/niosh/pdfs/7501.pdf, 8 pages, Aug. 15, 1994.

"Silica, Crystalline by IR" NIOSH Manual of Analytical Methods (NMAM), Fourth Edition, Method 7602, Issue 2, http://www.cdc.gov/niosh/pdfs/7602.pdf, 5 pages, Aug. 15, 1994.

"Silica, Crystalline in Coal Mine Dust, by IR" NIOSH Manual of Analytical Methods (NMAM), Fourth Edition, Method 7603, Issue 2, http://www.cdc.gov/niosh/pdfs/7603.pdf, 6 pages, Aug. 15, 1994.

"Software: OS-MLR" Optical Solutions, Inc., 2 pages, http://www.optical-solutions.com/software.html, website visited on Dec. 4, 2000.

"Spectral Subtraction" Galactic Industries Corporation, 2 pages, http://www.galactic.com/Algorithms/subtract.htm, website visited on Dec. 6, 2000.

"Spectrometer Drivers with XRFWIN" Tasker Applications, 2 pages, http://www.tasitechnical.com/tapp/spec.html, website visited on Nov. 1, 2001.

"USGS Spectroscopy Lab—Software" U.S. Geological Survey, a bureau of the U.S. Department of the Interior, http://speclab.cr.usgs.gov/software.html, 2 pages, website visited on Mar. 21, 2001.

"XRFWIN 3.0" Tasker Applications, http://www.tasitechnical.com/tapp/xrfwin.html, 3 pages, website visited on Nov. 1, 2001.

XFRWIN Screenshots, "Create Tube Spectrum Settings," "XFRWIN Demonstration for Windows," and "About XRFWIN," Tasker Applications, Kingston, Ontario, Canada, printed on Nov. 1, 2001, 1 page.

Banerjee et al., "Interpreting Multicomponent Infrared Spectra by Derivative Minimization," Society for Applied Spectroscopy, *Applied Spectroscopy*, vol. 45, No. 6, pp. 1047-1049, 1991, no month.

Cameron et al., "Precision in Condensed Phase Vibrational Spectroscopy," *Applied Spectroscopy*, vol. 36, No. 3, pp. 245-250, 1982, no month.

Friese et al., "Lignin Determination by FT-IR," Society for Applied Spectroscopy, *Applied Spectroscopy*, vol. 46, No. 2, pp. 246-248, 1992, no month.

Gillette et al., "Objective Criteria for Absorbance Subtraction," Society for Applied Spectroscopy, *Applied Spectroscopy*, vol. 38, No. 3, pp. 334-337, 1984, no month.

Griffiths et al., *Fourier Transform Infrared Spectrometry*, John, Wiley & Sons, Inc., pp. 230-239, 338-368, 1986, no month.

Ingle et al., *Spectrochemical Analysis*, Prentice-Hall, Inc., pp. 135-138, 1988, no month.

Kane et al., "Multiplexed Photometers for Online Analysis," (Brief Article) Gulf Publishing Co., *Hydrocarbon Processing*, vol. 79, Issue 5, p. 36, May 2000.

Morton, "Technology Advances Marking Milestones in Microscopy," *The Scientist*, vol. 11, No. 2, p. 18, Jan. 20, 1997.

Potts, *Chemical Infrared Spectroscopy*, vol. I: Techniques, John Wiley & Sons, Inc., pp. 155-203, 1963, no month.

Smith, *Fundamentals of Fourier Transform Infrared Spectroscopy*, CRC Press, Inc., pp. 7-11, 55-63, and 139-149, 1996, no month.

Thomas, *Calculus and Analytic Geometry*, Alternate Edition, Addison-Wesley Publishing Company, Inc., pp. 270-271, 1972, no month.

Trueba, "Mineral Identification and Abundance Analysis in Marine Sediments Using Infrared Reflectance Spectroscopy," Honors Thesis, Brown University, Providence, Rhode Island, 25 pages, May 6, 1996, http://www.public.asu.edu/~aknudson/thesis.html, website visited on Mar. 21, 2001.

Trueba, "Thesis, Trueba: Introduction," Honors Thesis, Brown University, Providence, Rhode Island, 11 pages, http://www.public.asu.edu/~aknudson/thesis/body.html, website visited on Mar. 21, 2001.

* cited by examiner

PRIOR ART

CHANGE SPECTRAL ANALYSIS PARAMETERS

REFERENCE FILE: C:\WIN_IR\PVC2MAY9.SPC

A RANGE BETWEEN 4000 AND 150 CM-1 WILL BE ENFORCED FOR INTEGRATION LIMITS. LEFT LIMIT IS TO BE GREATER THAN RIGHT LIMIT.

INTEGRATION LIMITS FOR QUARTZ

| | |
|---|---|
| LEFT LIMIT | 815 |
| RIGHT LIMIT | 770 |
| PEAK HEIGHT | 800 |

INTEGRATION LIMITS FOR KAOLIN

| | |
|---|---|
| LEFT LIMIT | 950 |
| RIGHT LIMIT | 900 |
| PEAK HEIGHT | 917 |

INTEGRATION LIMITS FOR LIMESTONE

| | |
|---|---|
| LEFT LIMIT | 895 |
| RIGHT LIMIT | 840 |
| PEAK HEIGHT | 877 |

INTERFERENT CHOICE: NONE ▼

ALGORITHMS — 1032

CHANGE REFERENCE — 1024

OK — 1012

CANCEL

CHANGE PARAMETERS FOR FLAGS

SIGNAL-TO-NOISE RATIO (SNR) FLAG

| | |
|---|---|
| NOISE MEASUREMENT REGION LEFT LIMIT | 640 |
| NOISE MEASUREMENT REGION RIGHT LIMIT | 600 |
| LOWEST ALLOWABLE SNR (>=3) | 3 |
| REGION TO MEASURE SIGNAL | QUARTZ ▼ |

1422

| | |
|---|---|
| QUARTZ MASS FLAG | [X] 1412 |
| LOWER LIMIT OF QUARTZ MASS (0-5000) | 0 |
| UPPER LIMIT OF QUARTZ MASS (0-5000) | 5000 |
| NEGATIVE PEAK AREA FLAG | [X] |
| PERCENT NEGATIVE PEAK AREA LIMIT (0-100) | 1 |

OK    CANCEL

```
┌─────────────────────────────────────────────────────────┐
│ ENTER CALIBRATION CURVE INFORMATION AND ANALYTE NAMES   │
│                                                         │
│              QUARTZ CAL. CURVE SLOPE (0-1)  [1]         │
│        QUARTZ CAL. CURVE Y INTERCEPT (-500 TO 500) [0]  │
│                                                         │
│              KAOLIN CAL. CURVE SLOPE (0-1)  [1]         │
│        KAOLIN CAL. CURVE Y INTERCEPT (-500 TO 500) [0]  │
│                                                         │
│           LIMESTONE CAL. CURVE SLOPE (0-1)  [1]         │
│     LIMESTONE CAL. CURVE Y INTERCEPT (-500 TO 500) [0]  │
│                                                         │
│                                                         │
│                   CHANGE ANALYTE NAMES                  │
│                                                         │
│              NAME OF ANALYTE #1  [QUARTZ]               │
│              NAME OF ANALYTE #2  [KAOLIN]               │
│              NAME OF ANALYTE #3  [LIMESTONE]            │
│                                                         │
│              [    OK    ]      [   CANCEL   ]           │
└─────────────────────────────────────────────────────────┘
```

```
REVIEW OF PARAMETERS TO BE USED

PVC REFERENCE SPECTRUM = C:\WIN_IR\PVC2MAY9.SPC

INTEGRATION LIMITS FOR QUARTZ
   LEFT X = 815  RIGHT  X = 770; PEAK HEIGHT MEASURED AT 800
               INTEGRATION LIMITS FOR KAOLIN
   LEFT X = 950  RIGHT  X = 900; PEAK HEIGHT MEASURED AT 917
              INTEGRATION LIMITS FOR LIMESTONE
   LEFT X = 895  RIGHT  X = 840; PEAK HEIGHT MEASURED AT 877

PEAK HEIGHT ALGORITHM = MAX
              BASELINE ENDPOINT ALGORITHM = MIN
              OPTIMIZATION WINDOW = 5 DATA POINTS
              INTERFERENT CORRECTION USED = NONE
 MANUAL SUBSTRACTION IS OFF  MANUAL SUBTRACTION FACTOR = 0

FLAGGING PARAMETERS
                NOISE MEASURED FROM 640 TO 600
                   LOWEST ALLOWED SNR = 3
                SIGNAL MEASURED IN REGION QUARTZ
                    QUARTZ MASS FLAG IS ON
            QUARTZ MASS LIMITS ARE FROM 0 TO 5000
                 NEGATIVE PEAK AREA FLAG IS ON
              NEGATIVE PEAK AREA LIMIT = 1 PERCENT
                  CALIBRATION CURVE INFORMATION
         QUARTZ CAL. CURVE: SLOPE = 1  Y INTERCEPT = 0
         KAOLIN CAL. CURVE: SLOPE = 1  Y INTERCEPT = 0
        LIMESTONE CAL. CURVE: SLOPE = 1  Y INTERCEPT = 0

OK            CHANGE PARMS           QUIT
```

CREATE ANALYTE NAMES

ENTER THE ANALYTE AND INTERFERENT NAMES.
LEAVE FIELDS FOR UNUSED ANALYTES/INTERFERENCES BLANK.

| | 1822 |
|---:|:---|
| NAME OF ANALYTE #1 | QUARTZ |
| NAME OF INTERFERENT #1 | KAOLIN |
| NAME OF ANALYTE #2 | |
| NAME OF INTERFERENT #2 | |
| NAME OF ANALYTE #3 | |
| NAME OF INTERFERENT #3 | |
| INTERNAL STANDARD NAME: | ABC (1842) |

[ OK ]   [ CANCEL ]

CHANGE SPECTRAL ANALYSIS PARAMETERS

A RANGE BETWEEN 40000 AND 10 CM-1 WILL BE ENFORCED FOR INTEGRATION LIMITS. LEFT LIMIT IS TO BE GREATER THAN RIGHT LIMIT. PEAK HEIGHT POSITION IS TO BE BETWEEN THE LEFT AND RIGHT LIMIT.

INTEGRATION LIMITS FOR QUARTZ
LEFT LIMIT [815]  RIGHT LIMIT [770]  PEAK HEIGHT [800]

INTEGRATION LIMITS FOR KAOLIN
LEFT LIMIT [950]  RIGHT LIMIT [900]  PEAK HEIGHT [917]

.
.
.
.
.
.

1920

INTEGRATION LIMITS FOR INTERNAL REFERENCE ABC:
LEFT LIMIT [ ]  RIGHT LIMIT [ ]  PEAK HEIGHT [ ]

1932 — ALGORITHMS    1924 — CHANGE REFERENCE

1912 — OK            CANCEL

```
┌─────────────────────────────────────────────────────────────┐
│ ENTER CALIBRATION INFORMATION                               │
│                                                             │
│                                                             │
│              [ANALYTE 1] CAL. CURVE SLOPE    [ 1 ]          │
│                                                             │
│         [ANALYTE 1] CAL. CURVE Y INTERCEPT   [ 0 ]          │
│                                                             │
│                                                             │
│           [INTERFERENT 1] CAL. CURVE SLOPE   [ 1 ]          │
│                                                             │
│      [INTERFERENT 1] CAL. CURVE Y INTERCEPT  [ 0 ]          │
│                                                             │
│      [INTERFERENT 1] PEAK RATIO FOR CORRECTION              │
│                                       FACTOR [ 0.5 ]        │
│                             •                               │
│                             •                               │
│                             •                               │
│                             •                               │
│                             •                               │
│                             •                               │
│                             •                               │
│                                                             │
│                     ANALYTE UNITS  [ MOLES/LITER ]          │
│                                                    ⬉ 2012   │
│                   CALIBRATION TYPE [ PEAK HEIGHT ▼ ]        │
│                                 2022⤴                       │
│             [     OK     ]           [   CANCEL   ]         │
│                                                             │
└─────────────────────────────────────────────────────────────┘
```

PEAK HEIGHT/AREA OPTIMIZATION AND SUBTRACTION

PEAK HEIGHT ALGORITHM — MAX ▼

BASELINE ENDPOINT ALGORITHM — MIN ▼

POINTS FOR MAX/MIN ALGORITHMS (AN ODD # <1000) — 3

AUTOMATIC SUBTRACTION [X]  ←2110

A.S. FACTOR OPTIMIZATION REGION LEFT LIMIT — 10

A.S. FACTOR OPTIMIZATION REGION RIGHT LIMIT — 10

MANUAL SUBTRACTION [ ]

MANUAL SUBTRACTION FACTOR (-5 TO 5) — 0

2112
[ OK ]    [ CANCEL ]

SYSTEMS AND METHODS FOR AUTOMATED QUANTITATIVE ANALYSIS OF DIGITIZED SPECTRA

RELATED APPLICATION DATA

This application is a U.S. national stage of PCT/US02/40315 filed Dec. 17. 2002, which was published in English under PCT Article 21(2), and which in turn claims the benefit of Tuchman et al., U.S. Provisional Patent Application No. 60/342,624, filed December 21, 2001.

TECHNICAL FIELD

The technical field relates to a variety of methods and systems directed to automated quantitative digitized spectral analyses, such as Fourier transform infrared spectroscopy analysis techniques.

BACKGROUND

Spectral analysis has emerged as an efficient and accurate tool for quantitative analysis. For example, given a physical sample of unknown composition, infrared spectral analysis can be used to determine the amount of a particular substance present in the sample.

Typically, a test process is performed on the sample, and an infrared spectrum is produced. The spectrum can then be analyzed via various mathematical techniques to generate output values indicating masses of various substances in the sample. The substances are sometimes called "analytes."

Some analytes are of particular interest because they are known to cause or aggravate disease. For example, exposure to quartz (i.e., crystalline silica) has long been recognized as a cause or aggravating factor for a variety of diseases, such as silicosis or coal worker's pneumoconiosis. Further, quartz is suspected of causing lung cancer. For the safety of persons working in an environment in which quartz is likely present (e.g., a mine), it is often desired to measure the airborne concentrations of quartz dust in the environment. Such measurement can be accomplished by analyzing the amount of quartz on filters that have been exposed to the environment (e.g., air sampling dust filters worn by the workers).

Thus, there are a number of laboratories across the world performing quantitative analyses of dust samples for quartz content. Infrared spectroscopy can be used to determine quartz mass. A laboratory may perform analyses on tens of thousands of samples per year. Such large scale analysis is expensive and may require many highly-skilled personnel. Due to misunderstandings relating to proper spectroscopy analysis procedure, unskilled personnel can easily introduce error into the process, and even skilled personnel can inadvertently introduce human error into the process.

Further, different laboratories may apply different techniques or use different equipment for performing quantitative analyses. As a result, it is difficult for laboratories to mutually share and implement a fully consistent method that determines the amount of quartz in samples and whether the amount present indicates risk to workers.

SUMMARY OF THE DISCLOSURE

In disclosed embodiments, quantitative analysis of digitized infrared spectra can be automated. Various user interfaces can be presented to acquire parameters related to the automated analysis.

In certain embodiments, a parameter-editing user interface is presented by which a user can view and edit parameters controlling automated analysis. The user interfaces can depict both the parameter value and an indication of its functionality (e.g., a name or other description) so that a user can easily edit the parameters without having to know the internal workings of the software or how the parameters are stored internally. Such an approach can be useful, for example, for avoiding having to edit a parameter file with a text editor. In this way, the process of performing an automated analysis can be simplified, errors avoided, and its accuracy improved.

In some embodiments, various user interfaces can be presented to guide a user through a parameter-setting process. In some instances, the user interfaces can serve to train the user, reducing the amount of training required from skilled personnel for a user to implement an automated analysis.

In disclosed embodiments, one or more suspect parameter conditions can be detected. Responsive to detection of a suspect parameter condition, an appropriate advisory can be displayed, and a parameter-editing user interface presented by which the suspect parameter condition can be corrected. Such an approach can be useful, for example, for avoiding automated analysis using parameters that are mathematically infeasible or impossible.

In certain embodiments, a suspect analysis condition can be detected. Responsive to detection of the suspect analysis condition, provided results can include a warning related to the suspect analysis condition. A parameter-editing user interface can include parameters controlling detection of suspect analysis conditions and whether a warning is provided. Such an approach can be useful, for example, to alert a user to possible problems with a spectrum or its analysis.

Parameters implemented in software can include a wide variety of parameters related to automated analysis and automated detection of suspect analysis conditions. For example, core absorbance band parameters (e.g., integration limits and peak position parameters) and algorithm selection parameters can be supported. Further, parameters related to signal-to-noise ratio monitoring and negative peak area monitoring can be implemented.

The software can support analyses utilizing an internal standard via a ratio factor parameter. For example, a known quantity of a reference analyte can be introduced into a sample, and the quantity of another analyte can be determined by comparison.

If desired, the parameters can be stored in a file. Such an approach can be useful, for example, for retrieving sets of previously-stored parameters. Also, inter- and intra-laboratory parameter sharing via the parameter sets can reduce variability in results. For example, a collection of laboratories can employ any of a variety of analytical protocols found mutually-agreeable and then adhere to the protocol in a highly uniform and standard way.

The foregoing and other features and advantages will become more apparent from the following detailed description of disclosed embodiments which proceeds with reference to the accompanying drawings.

BRIEF DESCRIPTION OF THE FIGURES

FIG. 10 is an exemplary graphical user interface for editing spectral analysis parameters.

FIG. 14 is an exemplary user interface for viewing and editing parameters relating to providing suspect analysis condition warnings.

FIG. 16 is an exemplary parameter-editing user interface for viewing and editing parameters related to calibration and analyte names.

FIG. 17 is an exemplary user interface for presenting a summary of parameters and their values to be used in an automated analysis.

FIG. 18 is an exemplary user interface for viewing and editing parameters related to analyte and interferent names.

FIG. 19 is an exemplary user interface for viewing and editing parameters related to spectral analysis.

FIG. 20 is an exemplary user interface for viewing and editing parameters related to calibration.

FIG. 21 is an exemplary user interface for viewing and editing parameters related to a quantitative analysis.

DETAILED DESCRIPTION OF EXEMPLARY EMBODIMENTS

Exemplary Methods for Automating Quantitative Analysis

Overview

Figure 1:
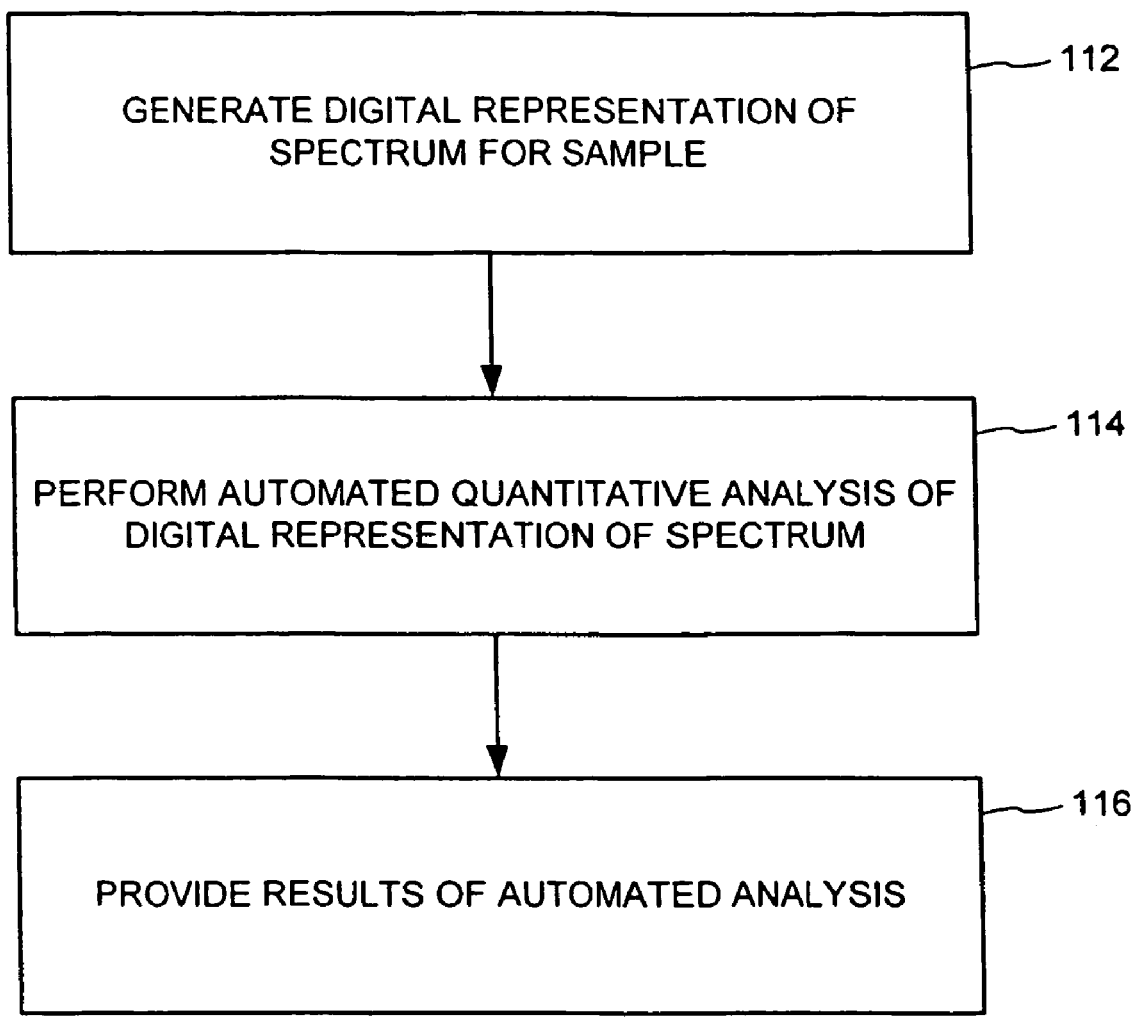
FIG. 1 is a flow chart showing an exemplary method for performing a quantitative analysis of a sample.

An overview of an exemplary method 100 for performing quantitative analysis of a sample (e.g., via an infrared spectroscopy technique such as a Fourier transform infrared or "FTIR" spectroscopy technique) is shown in FIG. 1. The sample can be any of a variety of materials or mixtures of materials, such as one or more analytes embedded in a filter.

At 112, a digital representation of a spectrum for the sample is generated. For example, a spectrometer and associated equipment can be used to produce a digital representation of a spectrum for the sample. Any of a wide variety of spectrometers and associated equipment can be used. In one embodiment, the digital representation takes the form of a data file containing information indicating a spectrum; however, other techniques can be used.

At 114, an automated quantitative analysis of the digital representation of the spectrum is performed (e.g., via an infrared spectroscopy technique such as a Fourier transform infrared spectroscopy technique). For example, quantification metrics (e.g., masses or concentrations) for one or more analytes present in the sample can be calculated by software.

At 116, results of the analysis are provided. For example, results indicating quantification metrics of one or more analytes in the sample can be displayed on a screen, printed, or stored in a file by software. Related information can be provided in the results to assist in evaluating results of the analysis.

Parameter Acquisition and Automated Quantitative Analysis

Figure 2:
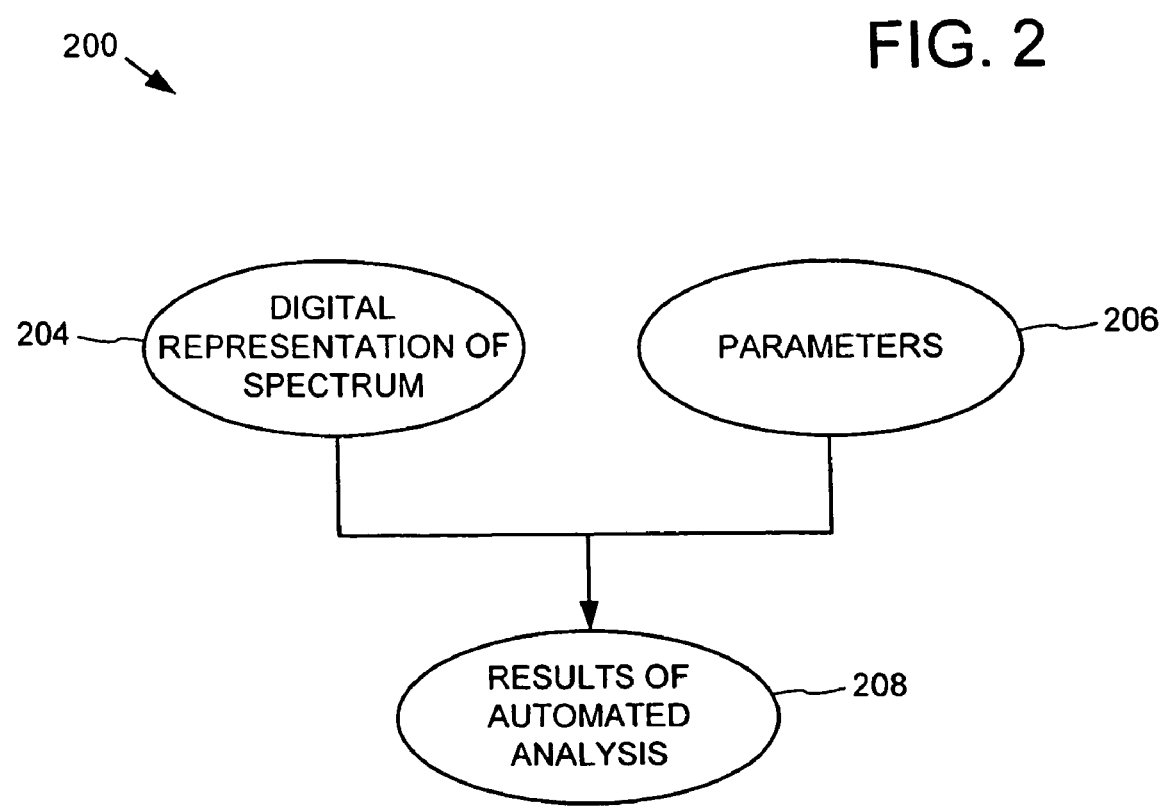
FIG. 2 is a data flow diagram showing an exemplary automated quantitative analysis of a spectrum.

FIG. 2 shows a data flow diagram 200 depicting an exemplary automated quantitative analysis of a spectrum. A digital representation of a spectrum 204 for a sample and various parameters 206 are used to generate results of the automated analysis 208. The parameters 206 can include an indication (e.g., a file name) of a digital representation of a reference spectrum, which, for example, can be subtracted from the digital representation of the spectrum 204 during analysis, if desired. The described data can be stored in computer-readable media (e.g., RAM, ROM, removable media, and the like) or acquired via a carrier wave (e.g., sent over a network, such as the Internet, an intranet, or the like).

Figure 3:
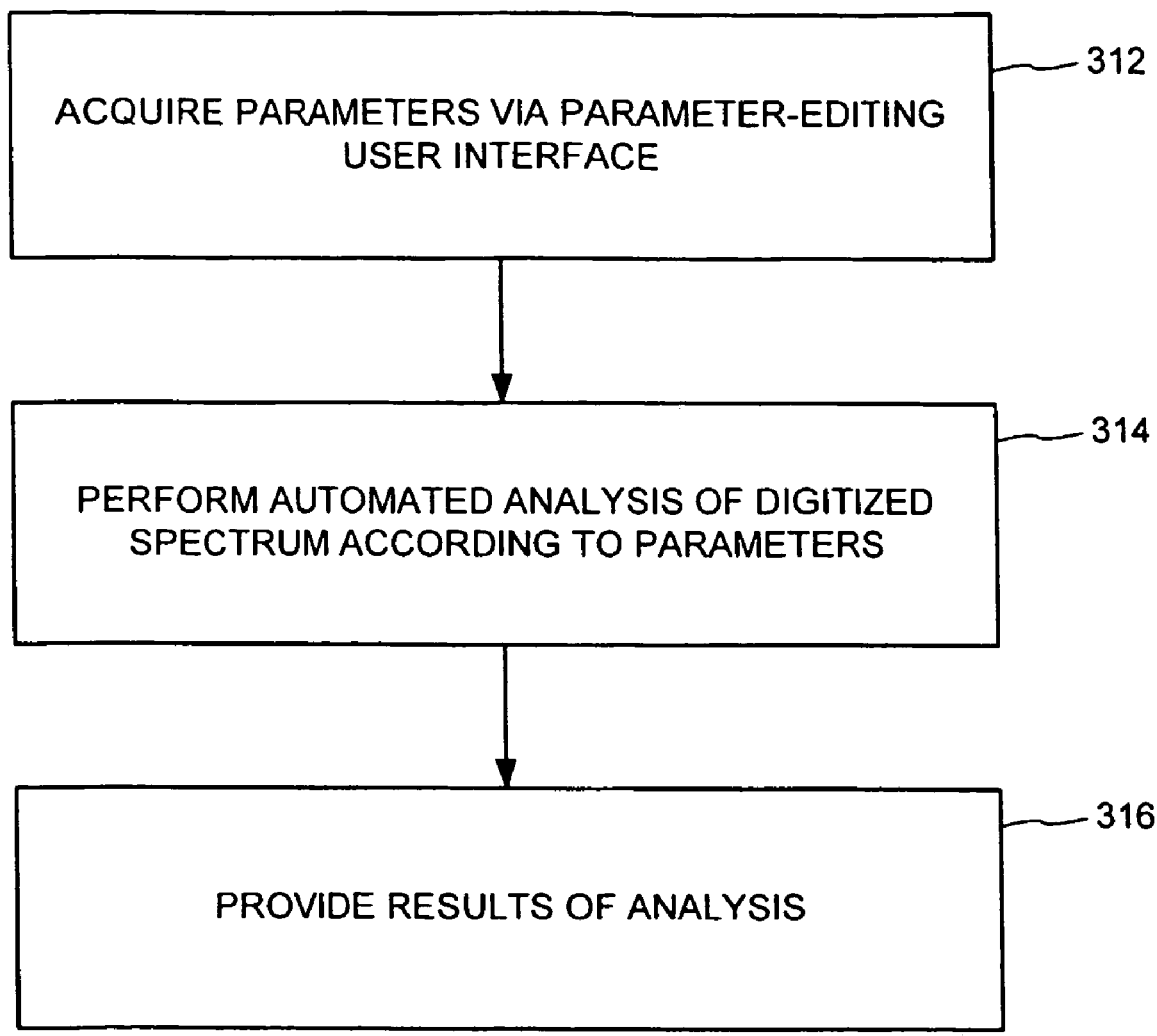
FIG. 3 is a flowchart showing an exemplary method for performing an automated quantitative analysis.

FIG. 3 shows an exemplary method 300 for performing an automated quantitative analysis (e.g., via an infrared spectroscopy technique such as a Fourier transform infrared spectroscopy technique). At 312, parameters are acquired via a parameter-editing user interface. For the sake of convenience, the parameters can be associated into a file, which allows easily switching between previously-stored parameter sets. In such a case, the parameters can be simply loaded from the file. Then, at 314, an automated analysis of a spectrum (e.g., via an infrared spectroscopy technique such as a Fourier transform infrared spectroscopy technique) for a sample is performed via the parameters. At 316, the results of the analysis are provided.

Figure 4:
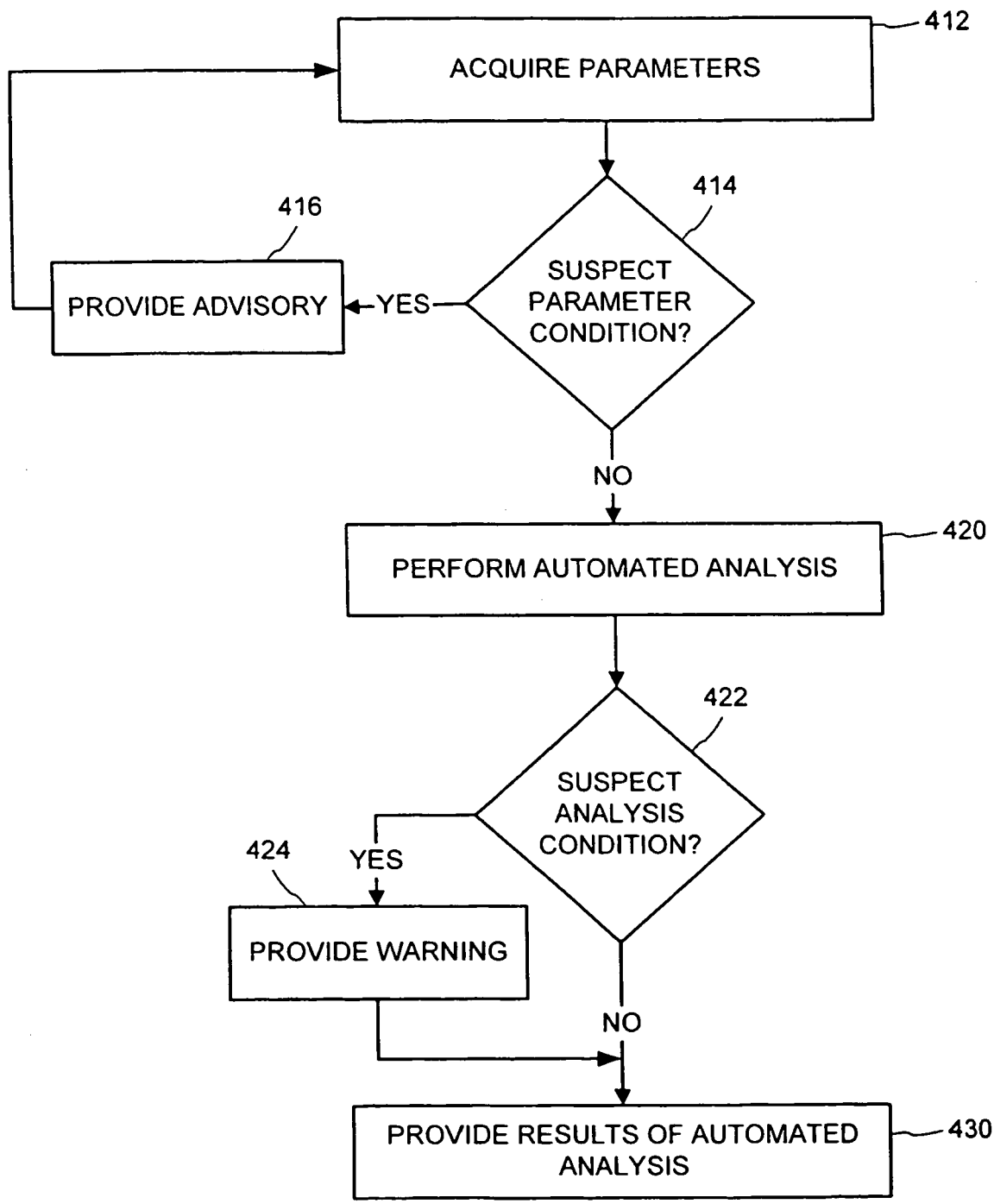
FIG. 4 is a flow chart showing an exemplary method for performing an automated quantitative analysis, including detecting suspect parameter conditions.

FIG. 4 shows another exemplary method 400 for performing an automated quantitative analysis (e.g., via an infrared spectroscopy technique such as a Fourier transform infrared spectroscopy technique). At 412, parameters are acquired. The parameters can be acquired in a number of ways, such as via a user interface or by retrieving them from a file. To assist in organizing acquisition of parameters and to guide a user through the parameter acquisition process via a set of parameter-editing graphical user interfaces, parameters can be grouped into parameter families and parameters in the same family can be displayed together in the same parameter-editing graphical user interface. The user interfaces can depict both the parameter value and its name, description, or significance. Guidance on possible parameter values (e.g., a valid range of values) to enter can also be presented. Choices for various parameters can be displayed as drop-down pick lists or pop up menus. If desired, Boolean parameters can be modified via checkboxes.

At 414, suspect parameter conditions, if any, are detected. Detection can take place upon user entry of a parameter or after acquisition of a number of parameters. At 416, if a suspect parameter condition is detected, an advisory is provided. Such an advisory can be provided in a variety of ways, such as by a dialog box indicating the suspect parameter condition. After dismissal of the advisory, a user can be immediately provided with the opportunity to modify the related parameter via a parameter-editing graphical user interface at 412. Processing can be inhibited so that automated analysis will not take place until the suspect parameter condition is corrected.

If no suspect parameter conditions are detected, an automated analysis as indicated by the parameters can be performed on one or more spectra at 420. At 422, suspect analysis conditions, if any, can be detected. At 424, if a suspect analysis condition was detected, an indication is provided. Such an indication can be provided in a variety of ways, such as by a text message or other indication embedded within results. Detection of a suspect analysis condition need not interrupt the analysis. However, the software can be configured so that the analysis is interrupted. For example, the analysis may require changing parameter values (e.g., via acquiring parameters 412) before continuation.

Additional or fewer branches in the flow can be provided. For example, in some cases, a link from providing a warning 424 to acquiring parameters 412 can be implemented (e.g., if the warning relates to integration limits being too close in relation to a provided number-of-points parameter).

At 430, results of the automated analysis are provided. Results can be provided in a variety of ways, for example by displaying on a video screen, printing, or storing in a file by software.

For convenience of the user, a graphical user element (e.g., a checkbox) can be provided by which a user can toggle (e.g., turn off) automatic hard copy printing of results. In such a case, electronic versions of output can still be saved.

Exemplary System for Automating Quantitative Analysis

Figure 5:
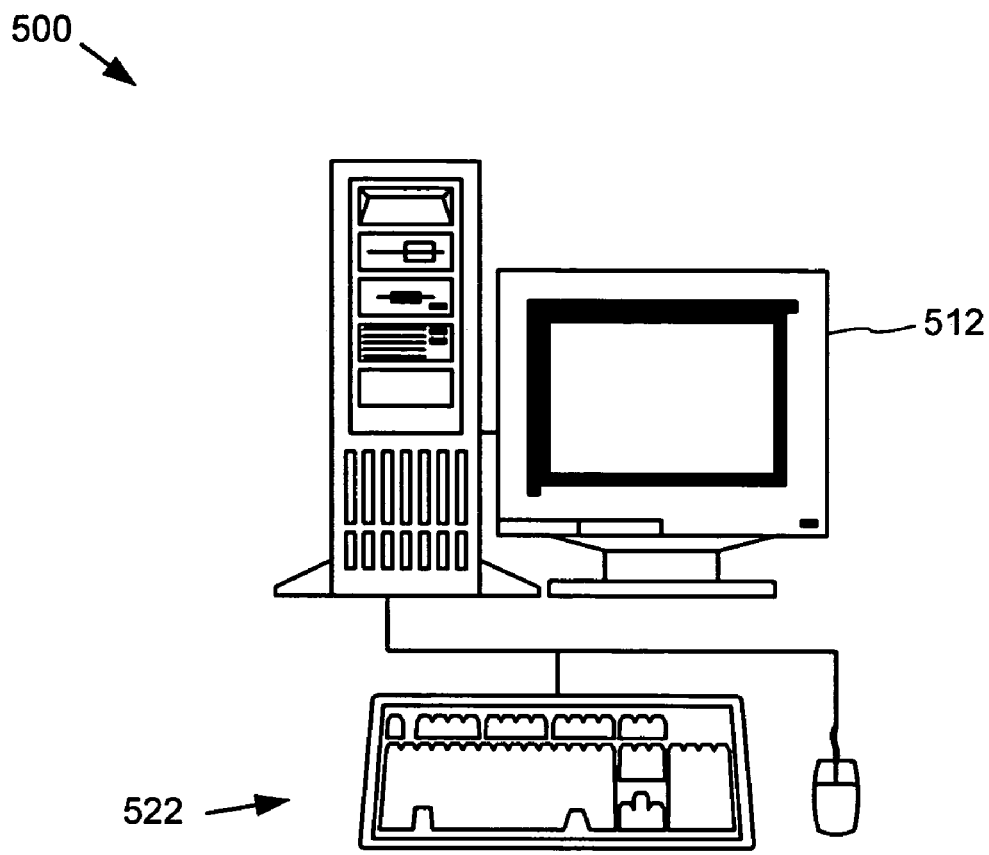
FIG. 5 is an illustration of an exemplary prior art system for carrying out automated quantitative analysis of a spectrum.

FIG. 5 shows an exemplary system 500 for carrying out an automated quantitative analysis of a spectrum (e.g., via an infrared spectroscopy technique such as a Fourier transform infrared spectroscopy technique). The system 500 includes a computer system 512, which typically includes a video monitor and user input devices 522, such as a keyboard and a pointing device (e.g., mouse, trackball, or the like).

Any number of computer systems (e.g., a general-purpose computer system) running any number of operating systems capable of supporting the analysis software can be used. Digital representations of spectra can be acquired (e.g., with a spectrometer) via the system 500, or by another apparatus and then analyzed by the system 500.

The system 500 is operable to execute computer-executable instructions encoded on a computer-readable medium (e.g., RAM, ROM, removable media, and the like) or acquired via a carrier wave (e.g., sent over a network, such as the Internet, an intranet, or the like).

Exemplary Parameters

A wide variety of parameters can be supported by the software. Parameters can include those that affect the automated analysis and those that serve to control detection of conditions and display of warnings provided as part of analysis results.

The parameters listed below can be presented by one or more parameter-editing user interfaces, by which a user can adjust the values. Such user interfaces can guide a user through the parameter-acquisition process and thus simplify the automated analysis process, reduce errors, and improve accuracy. For example, a parameter-editing user interface can display both a parameter value and its name, description, or significance on the parameter-editing user interface. Guidance on possible parameter values (e.g., a valid range of values) to enter can also be presented. Further, some parameters can be chosen from lists of possible values presented by a parameter-editing interface. Boolean parameters can be modified by activating a checkbox if desired.

Spectral Analysis Parameters

Spectral analysis parameters can include any of a wide variety of parameters modifiable by a parameter-editing user interface to control automated analysis of one or more spectra. In some cases, if a suspect parameter condition is detected in the spectral analysis parameters, an advisory is provided and the user is given an opportunity to adjust one or more parameters related to the suspect parameter condition by automatic presentation of an appropriate parameter-editing user interface for correcting the suspect condition.

Spectral Analysis Parameters: Core Absorbance Band Parameters

Exemplary spectral analysis parameters include core absorbance band parameters. Such parameters can include a left integration limit, a right integration limit, and a peak position (sometimes called "peak height" or shown as "peak height" by user interfaces) for an analyte. In described embodiments, the left limit is to be greater than the right limit, but another convention can be used. More than one set of core absorbance band parameters (e.g., three sets of parameters for three analytes) can be supported by software. In some implementations, the peak position parameter is unnecessary.

In some examples, the core absorbance band parameters can indicate light frequencies in wavenumbers (reciprocal centimeters). However, other forms of spectroscopy can use other units. During automated analysis, the left and right limits can be used to calculate a baseline, and the peak position is taken to be a location where peak height above the baseline is calculated to generate a quantitative value indicating mass of an analyte. Alternatively, the spectrum trace above the baseline can be integrated and the area used as a basis for quantitation of the analyte. The analysis can proceed according to any of a number of algorithms, and the analysis can be further modified in a number of ways, such as by correcting for interferents. In some implementations, an analysis can proceed without need for a peak position parameter.

If desired, the software can automatically correct integration limits so that they fall within a predetermined range (e.g., between 4000 and 150 $cm^{-1}$). In such a case, if a number greater than the upper limit (e.g., 9000) is typed for a value, the value can be rounded down to the upper limit (e.g., 4000) by the software.

The software can check that the left integration limit for an analyte is greater than the right integration limit for the analyte. If not, a suspect parameter condition is indicated, and a dialog box can be displayed so indicating. After the user acknowledges the dialog box, a parameter-editing user interface for changing the integration limits can be immediately displayed by the software so the user can correct the error.

Similarly, the specified peak position can be checked by the software to be sure it is within the left and right limits. If not, an appropriate dialog box can be displayed. After the user acknowledges the dialog box, a parameter-editing user interface for changing the integration limits and/or peak position can be immediately displayed by the software so the user can correct the error.

Spectral Analysis Parameter: Interferent Choice

Another spectral analysis parameter can enable specification of an analyte as an interferent. Interferent correction can then take place based on the interferent selected, if any. The list of possible interferents can be presented by the parameter-editing user interface, and the user can choose from the list. Alternatives can be implemented whereby the interferent list and related parameter are not used.

Spectral Analysis Parameter: Reference Spectrum

Another spectral analysis parameter can enable specification of a reference spectrum. Such a feature can be helpful if the sample being analyzed is carried on a medium such as an air sampling dust filter. For example, a spectrum for a blank PVC filter can be specified. Alternatively, some other polymer filter spectrum (e.g., for a GELMAN DM METRICEL 450 filter of the Gelman Instrument Company of Ann Arbor, Mich.) can be used. Also, the absorbance spectrum of a KBr pellet or empty sample compartment could also be used as a reference. During automated analysis, the reference spectrum can be subtracted from the spectra being analyzed.

As a practical matter, the reference spectrum typically should be high quality and relatively noise-free to improve results. Also, the spectrum typically should be representative of filters used in preparing standards and samples for analysis.

The filter reference spectrum can be specified by providing a path name to a file on the computer system on which the software executes. A user-interface feature can be used to interactively select a filter spectrum (e.g., file) out of those listed.

During automated analysis, the reference spectrum can be subtracted by the software from spectra being analyzed. The reference spectrum can be subtracted to minimize residual peaks in a particular range (e.g., 600–640 $cm^{-1}$). The range can be modified (e.g., by editing a program line or via a graphical user interface).

The software can check to see if the specified sample and reference spectra exist. If not, an indication (e.g., dialog box) can be displayed, and the software can provide the user with an opportunity to correct the error by immediately displaying a parameter-editing user interface that includes a user interface element for specifying the correct spectrum (e.g., by specifying a file name or choosing from those listed).

Spectral Analysis Parameter: Peak Height Algorithm Choice

A spectral analysis parameter can be provided for selecting an algorithm to be applied when locating the top of an analyte peak for peak height measurement. An algorithm (e.g., Default, Max, or Center of Mass) can be specified by choosing from those listed by a parameter-editing user interface.

During automated analysis, a Default algorithm can use the peak position parameter value specified as a fixed location where peak height is measured. A Max algorithm can measure a peak height as the maximum absorbance point found in a window of data points centered at the specified peak position parameter value. The width of the window can be adjusted by a number-of-points parameter.

A Center of Mass algorithm can calculate a peak top using the peak position and number-of-points parameters to find the wavenumber location that is the absorbance-weighed center of mass of the peak.

If the position determined by the Default or Center of Mass algorithms falls between actual data points, linear interpolation can be used to calculate peak height.

Provided results can indicate one or more peak positions and peak heights, as well as the algorithm and parameters used to find them.

Spectral Analysis Parameter: Baseline Endpoint Algorithm Choice

A spectral analysis parameter can be provided for selecting an algorithm to be applied when locating baseline endpoints for a peak. The algorithms can come from any of a variety of sources. For example, custom algorithms can be constructed, or pre-programmed ones (e.g., from Thermo Galactic of Salem, N.H.) can be used. An algorithm (e.g., Default, Min, or Find Peak) can be specified by selecting from those listed by a parameter-editing user interface.

During automated analysis, a Default algorithm can use the left limit and right limit parameter values specified as fixed locations for the endpoints. A Min algorithm can determine endpoints by looking for minimum absorbance values in windows of data points (e.g., adjustable by the number-of-points parameter) centered at the specified integration limit values.

A Find Peak algorithm can find left and right peak edges by starting at the specified peak position parameter value entered for an analyte and then finding points to the left and right of the specified position where the slope equals zero (i.e., a point that has a positive slope with an adjacent point on one side and negative slope with an adjacent point on the other side). Such an algorithm is available from Thermo Galactic of Salem, N.H.

After baseline endpoints are determined, the points become the left and right integration limits used during automated analysis by the software. Results can explicitly indicate the baseline endpoint positions, as well as the algorithm and other parameters chosen to find them.

Spectral Analysis Parameter: Number-of-Points

As described with reference to the algorithms above, a number-of-points parameter can be provided to adjust the size of a data point window to be used for the algorithms. If both peak position and baseline endpoint optimization algorithms are used, the same size window can be used for both algorithms. Typically, the parameter is required to be odd. The software can validate the number by checking to see if it is odd. If it is not odd, an advisory can be provided, and the software can then present a parameter-editing user interface by which the parameter can be corrected. Similarly, the number can be required to be within a specified range (e.g., 1–999).

If the Min baseline endpoint algorithm is chosen, the parameter can be required to not exceed half the number of data points in an entire peak. Otherwise, the two windows may overlap or span the entire peak, leading to incorrectly derived baseline endpoints. During automated analysis, the number of data points can be checked by the software. If the parameter does not conform (e.g., the number of data points in the window is not less than half the number of data points in an analyte peak, as determined by the distance between integration limits), an error message can be displayed. The message can indicate how far apart the integration limits for a particular analyte should be. After displaying the message, the software can then present a parameter-editing user interface by which the integration limits can be adjusted or the number-of-points value can be adjusted in a related user interface.

Further Information Regarding Min, Max, and Center of Mass Algorithms

The starting data points for the Min algorithm can be the integration limits indicated by the right limit and left limit parameters. For example, if the Min baseline endpoint algorithm is chosen, and the left limit parameter indicates 3000 cm$^{-1}$ and the number-of-points parameter indicates five points, the minimum will be searched for at two data points above and two data points below 3000 cm$^{-1}$.

The Min, Max, and Center of Mass algorithms can use the same size optimization window width. The baseline endpoint algorithm calculation can take place before that for peak height. If so, the baseline algorithm runs first to find the endpoints, then the peak height algorithm runs to find and measure the peak height above the baseline.

Peak heights measured using different algorithms may be different due to differences in derived peak or baseline endpoint positions, which can come into play when comparing data derived from different analytical procedures. For difficult peaks, such as shoulders or peaks that share a common baseline, it may take trial and error (e.g., changing the spectral analysis parameters) to achieve desired results.

Further Information Regarding the Find Peak Algorithm

After an initial peak position parameter is specified for an analyte, the first spectral minima to the left and right of the point are then typically located. However, there may be minima in a peak that are not actual peak edges (e.g., shoulder or interferent peaks). If so, the Find Peak algorithm may incorrectly identify such minima as peak edges. Such a scenario can be avoided by giving the algorithm two assigned starting points on the downward sloping sides of a peak.

Further, problems can occur if the initial point given on the peak is itself a peak minimum. Again, adjusting the point first given to the algorithm helps with such problems.

Spectral Analysis Parameter: Manual Subtraction

Automatic subtraction can be used to subtract a specified spectrum (e.g., stored in a reference file) by an automatically determined factor. To avoid the automatically applied algorithm used to subtract a specified reference file, a parameter can be used to specify a manual subtraction technique. A manual-subtraction-factor parameter can be specified to indicate a factor to be applied to a reference spectrum for subtraction. The factor can be limited to a range (e.g., −3 to 3). If no subtraction is desired, a factor of zero (e.g., with any reference spectrum specified) can be used. Alternatively, a graphical user interface element (e.g., a checkbox) can be presented to toggle both automatic and manual subtraction off.

Spectral Analysis Parameters: Calibration Parameters

Various parameters can be specified by a parameter-editing graphical user interface to calibrate results/readings from the equipment (e.g., spectrometer) being used. The values of such parameters are typically experimentally determined for a particular spectrometer, analyte, and sample type from which spectra are collected.

Sets of parameter values can be associated with particular analytes. For example, a calibration line slope and intercept can be specified for an analyte.

A simplified analysis can be implemented by specifying zero values for slopes and intercepts for some (e.g., all but one) of the analytes. Limits on calibration line slopes (e.g., 0–1) and intercepts (e.g., −500–500) can be enforced by various means. Units are typically absorbance per microgram for the slopes (the Y-axis is typically absorbance).

Additionally, a calibration parameter can be presented for selecting between peak height and peak area quantitation of analytes.

Spectral Analysis Parameter: Analyte Names

The analyte and reference material names can be adjusted via a parameter-editing user interface. The changed names are propagated to other parts of the software (e.g., parameter acquisition and provided results). In one example, one reference and three analyte names are supported, but fewer or more could be implemented.

Suspect Analysis Condition Detection Parameters

Various other parameters can be used to control when the software provides a warning that a particular analysis is suspect. The parameters can be modified by a user via a parameter-editing user interface. The parameter-editing user interface can present both the parameter and a description of the suspect analysis condition to which the parameter is related. When results are provided, a warning (e.g., text message) can be provided in the results to indicate whether an analysis is suspect (e.g., the data failed a test as specified by the suspect analysis condition detection parameters). Results related to a suspect analysis may themselves be suspect.

In addition, suspect parameter conditions can be detected in the suspect analysis condition detection parameters. As with the spectral analysis parameters, the software can display an advisory and then a parameter-editing user interface by which the user can correct the suspect parameter condition.

Suspect Analysis Condition Detection Parameters: Signal-to-Noise Ratio Parameters An analysis may be suspect if it is based on a spectrum with an unacceptable signal-to-noise ratio, which typically indicates poor infrared spectra quality. Various parameters can be adjusted to control observation of signal-to-noise ratio and whether a warning is provided to indicate a suspect analysis due to unacceptable signal-to-noise ratio.

Left limit and right limit signal-to-noise (SNR) parameters can be specified to indicate wavenumber points defining the region where peak-to-peak noise will be measured. Typically, a peak-free portion of the spectrum close to the signal region is specified.

A lowest-allowable-SNR parameter can be used to define a minimum allowable signal-to-noise ratio for spectrum evaluation. A signal-to-noise ratio below the specified value indicates failure. Typically, failure indicates the mass of analyte present is too low for accurate quantitation, or the spectrum's noise is too high. The parameter can be controlled by a parameter-editing user interface so that a minimum value (e.g., 3) is enforced.

A region-to-measure-signal parameter can also be specified to indicate the signal portion to be used for the signal-to-noise calculation. Choices can be provided for various analytes as well as None. The None choice can turn off the indications of a suspect analysis condition related to the signal-to-noise ratio (e.g., the calculations can still be performed, but no test is applied and provided results can indicate results of the calculations but indicate that no test was applied).

If an analyte is chosen, the peak height measured in the selected region (using elsewhere determined baseline endpoints and peak position) can be used as the signal in the signal-to-noise calculation. The magnitude or height ratio is determined with reference to the peak-to-peak noise measured in the region defined by the left limit and right limit SNR parameters.

The software compares the calculated signal-to-noise ratio to the lowest-allowable-SNR parameter. Regions used to calculate the signal-to-noise ratio, as well as whether the comparison failed, are included in provided results for a spectrum. Analysis need not be interrupted if the comparison fails.

During parameter entry, if the software detects that the left limit SNR parameter is not greater than the right limit SNR parameter, a dialog can be provided to so indicate, and the software can responsively present a parameter-editing graphical user interface by which a user can correct the error.

Suspect Analysis Condition Detection Parameters: Analyte Mass Parameters

Parameters related to monitoring mass can be implemented to control whether a warning is provided as part of results. First, a parameter can be used to control whether an analyte mass test is enabled (e.g., via a Boolean parameter).

If the test is enabled, other parameters (e.g., an upper limit and lower limit parameter) can be consulted to determine if an analyte (e.g., the primary analyte) has a mass within the specified limits. If not, a warning can be provided in the results. Such a warning can be useful to indicate, for example, that the limits of linearity have been reached or that detector saturation has occurred. If the analyte is within the limits, the results can so indicate.

Alternatively, a test based on magnitude of absorbance can be enforced (e.g., via lower level and upper level of absorbance parameters). In this way, an absorbance range test can be performed.

Suspect Analysis Condition Detection Parameters: Negative Peak Area Parameters

Parameters related to monitoring for a negative peak area can be implemented to control whether a warning is provided as part of the results. First, a parameter can be used to control whether a negative peak area test is enabled (e.g., via a Boolean parameter).

If the test is enabled, other parameters (e.g., a percent-negative-peak-area-limit parameter) can be provided to determine whether analytes fail the test. An analyte having more than the specified area (i.e., peak area below the baseline) fails the test. Test failure may indicate poorly chosen baseline endpoints. A range (e.g., 0–100 percent) can be enforced by the software for the percent-negative-peak-area-limit parameter.

A warning indicating failure of the negative peak area test can be provided in results per analyte to indicate whether each analyte failed or passed the test. If no test is applied, the results can so indicate.

Parameter Families

For the sake of convenience and to aid in guiding a user through the parameter-acquisition process, parameters can be grouped into families for presentation in a graphical user interface.

For example, a basic spectral analysis family can include core absorbance band parameters (e.g., analyte integration limits and peak position parameters). An analysis customization family can include a choice of algorithms for optimizing peak height positions and baseline endpoints as well as a number-of-points parameter. A calibration family can include parameters related to slopes and intercepts for analytes. A flag family can include parameters for controlling warnings related to suspect analysis conditions.

In some cases, not all parameters related to a parameter family will appear on a single user interface, but might all be accessed by first activating a single user interface element. Another user interface element might be activated to examine subfamilies of the parameters. For example, spectral analysis parameters might belong to a family, and algorithm-specifying parameters can belong to a subfamily within the spectral analysis family.

Parameter Files

Parameters can be stored in one or more files. For the sake of convenience, a set of parameters might be stored under a single name (e.g., in a single file) so that they can be easily retrieved for future use. Parameters in a parameter file can be edited without a user having to directly or separately access the parameter file (e.g., without using a text editor or a separate program). For example, a user can load the parameters and edit them via the provided graphical user interfaces, which display the parameter and a description of the parameter (e.g., a name of the parameter). Guidance concerning the parameter can also be presented by the user interfaces.

Alternatively, a parameter file can be created anew (i.e., from scratch) via provided graphical user interfaces. In this way, the user can be guided and assisted while specifying the parameters. Accordingly, errors related to erroneous parameters are reduced, and parameter sets can be shared among users via parameter files.

Switching between different sets of parameters can be easily accomplished by storing the sets in different parameter files. Thus, rapid switches between different types of analyses can be achieved.

Further Information

To achieve desired results, it may be advantageous to adopt various analysis methods described in publications available from various sources. For example, in the case of quartz (crystalline silica) analysis by infrared spectroscopy, the MSHA Method P-7 is provided by the U.S. Department of Labor, Mine Safety and Health Administration. The NIOSH Method 7602 and NIOSH Method 7603 are provided by the Centers for Disease Control and Prevention, National Institute for Occupational Safety and Health. The HSE Method MDHS 37 is a method used by Great Britain's Health and Safety Execute in the Occupational Medicine and Hygiene Laboratory. Other methods can be used for quartz, and other analytes can be analyzed.

Exemplary Methods and Systems for Performing the Quantitative Analysis

Any of a number of techniques for applying quantitative analysis can be utilized during automated analysis. In the following illustrated embodiments, a Fourier transform infrared spectroscopy technique is applied; however, any of a variety of other techniques involving digital output (e.g., digitized spectra or other spectral data) can be used with any of the methods and systems (e.g., user interfaces) described herein. Customization of the analysis can be achieved by modifying the parameters. Typically, a mass for one or more analytes is calculated and indicated in provided results. The illustrated methods and systems can be used for analyzing digital spectra associated with samples containing quartz to determine the mass of quartz contained in the sample, but the methods and systems can be applied to additional or other analytes.

Exemplary Software Architecture

Figure 6:
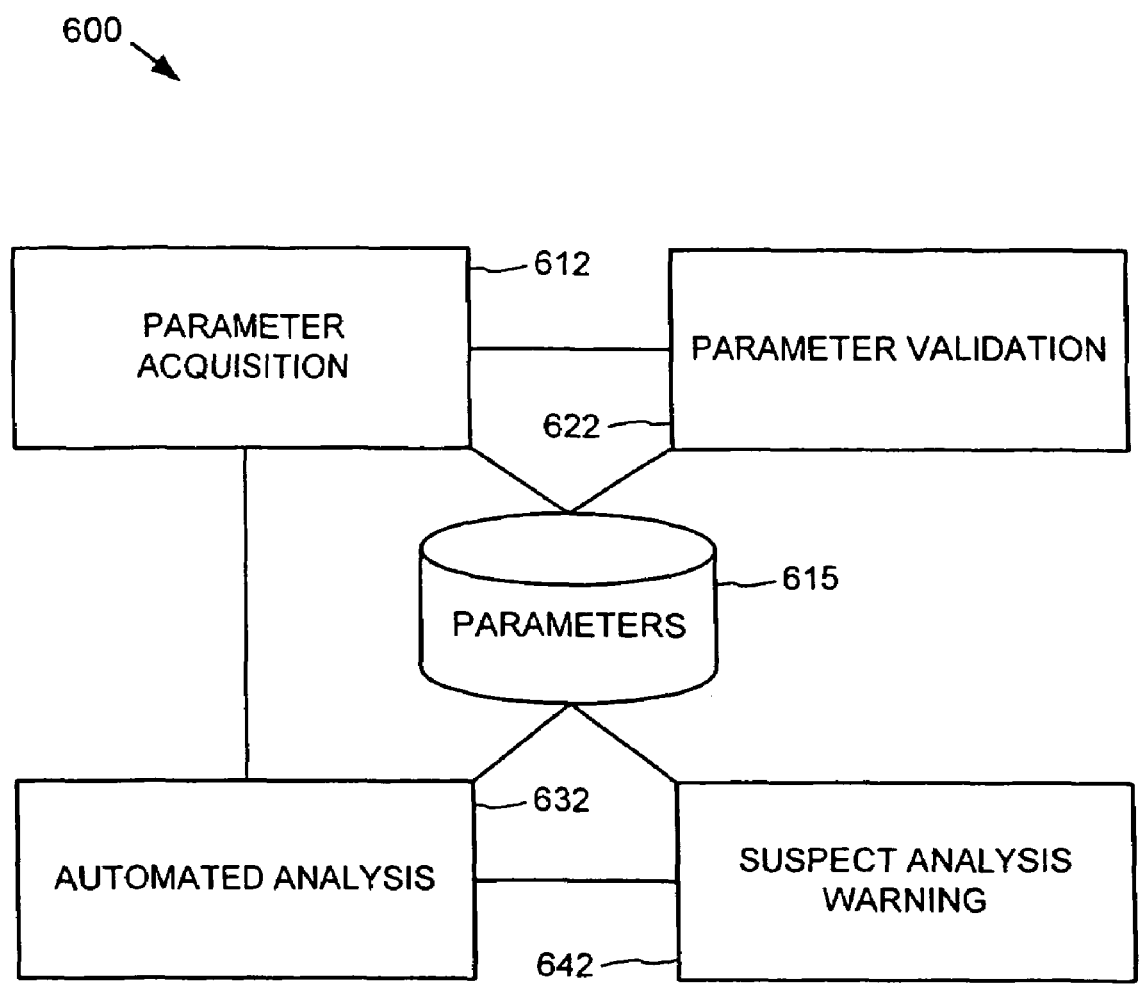
FIG. 6 is a block diagram showing an exemplary software architecture for carrying out automated quantitative analysis of a spectrum via an infrared spectroscopy technique.

FIG. 6 is a block diagram showing an exemplary software architecture 600 for carrying out automated quantitative analysis of a spectrum via a Fourier transform infrared spectroscopy technique. A parameter acquisition module 612 includes functionality related to acquiring parameters 615 (e.g., stored in memory), including presenting parameter-editing graphical user interfaces by which parameters can be edited. Linked to or contained within the parameter acquisition module 612 is a parameter validation module 622, which includes functionality for detecting suspect parameter conditions, displaying advisories related thereto, and directing the parameter acquisition module 612 to present an appropriate parameter-editing graphical user interface for correcting a condition related to the advisory.

An automated analysis module 632 includes functionality related to performing an automated analysis of a spectrum according to the parameters 615. Linked to or contained within the automated analysis module 632 is a suspect analysis warning module 642, which includes functionality for detecting and indicating suspect analysis conditions as controlled by the parameters 615.

The connections between modules are exemplary only. There may be more or fewer connections. For example, a connection between 642 and 612 may also exist.

In one implementation, the software is implemented in the ARRAY BASIC programming language and is launched from within the GRAMS/32 program developed by Thermo Galactic of Salem, N.H. The GRAMS/32 program can run on a computer having the WINDOWS operating system of Microsoft Corporation of Redmond, Washington. Alternatively, other languages and operating systems can be used.

Spectra can be provided in the GRAMS/32 file format (*.SPC) or can be imported into the GRAMS/32 program. Autosubtraction can be performed by a separate program (e.g., "AUTOSUBR.AB"). In other implementations, other formats or conventions can be used.

Operation of Exemplary Software

Operation of exemplary software implementing various features described above can proceed as described below. Alternatively, variations, including different user interfaces and sub- or super-sets of the illustrated parameters can be implemented. Further, the presentation order and number of various user interfaces can be varied in alternative implementations.

Spectral Files

Figure 7:
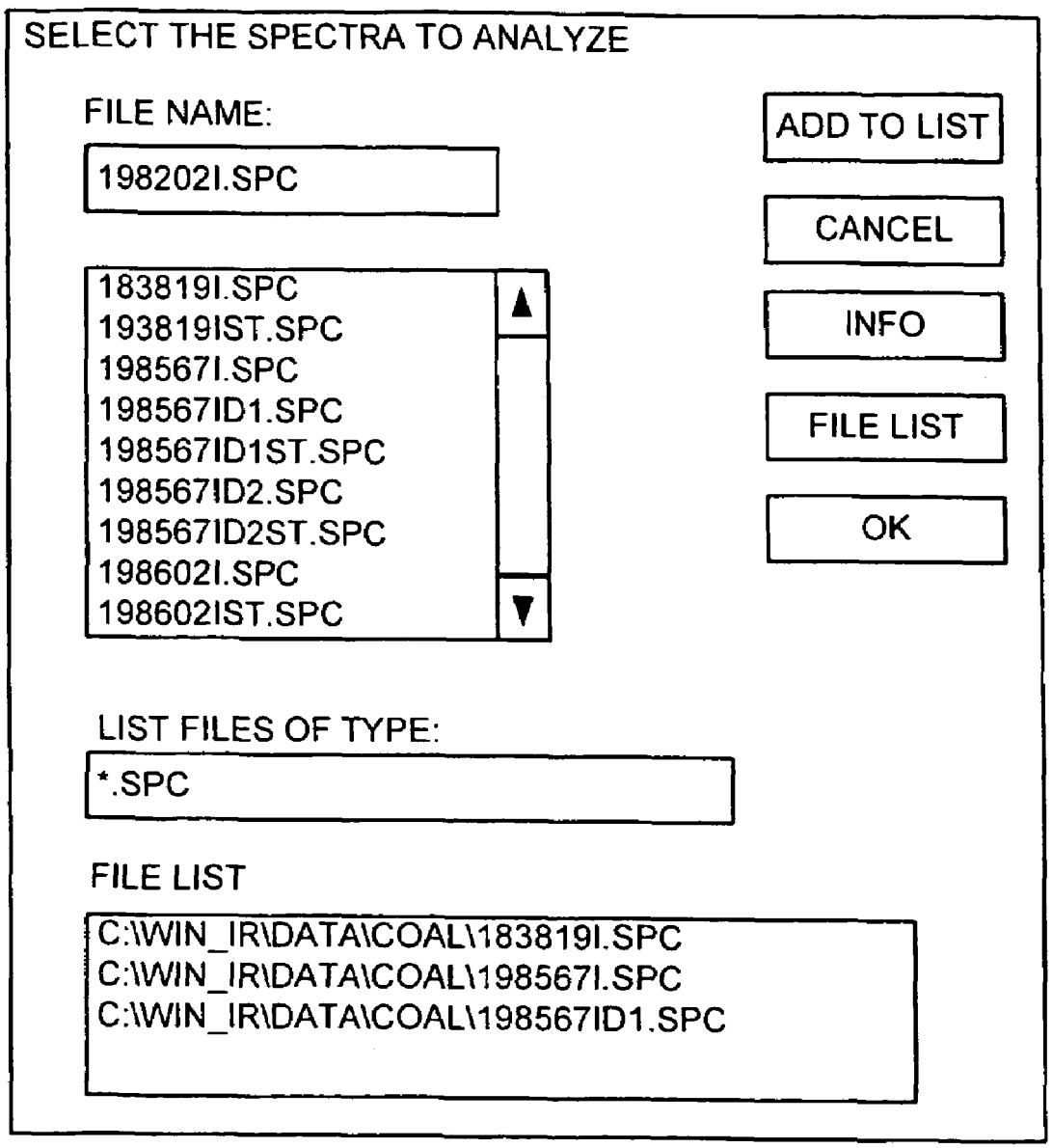
FIG. 7 is an exemplary graphical user interface for specifying spectra to be analyzed.

FIG. 7 shows an exemplary graphical user interface 700 for specifying one or more spectra to be analyzed. A user can choose one or more files having spectral information to be analyzed. The user interface 700 can vary in other implementations and can be dependent upon the underlying supporting software (e.g., application software in which the technologies are implemented or the operating system in which such software is executed). Next, parameters can be acquired.

Parameter Acquisition

Figure 8:
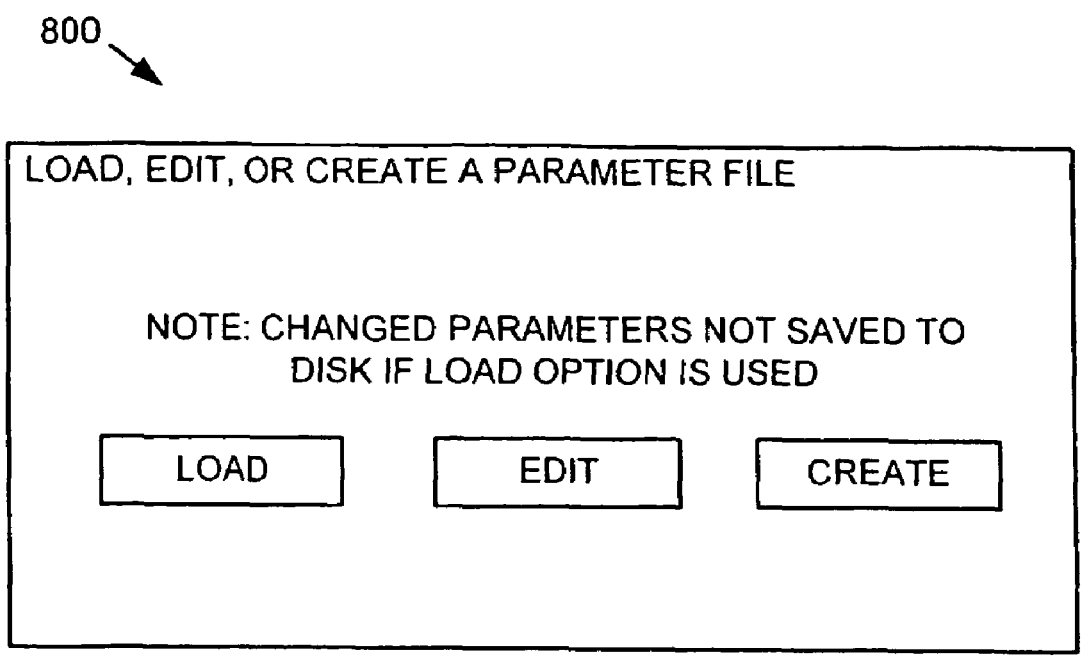
FIG. 8 is an exemplary graphical user interface for indicating a source for parameters.

FIG. 8 is an exemplary graphical user interface 800 for indicating a source for parameters. A new parameter file can be created. Newly-entered parameters are then stored in the file. A previously-stored parameter file can be loaded, or a previously-stored one can be loaded for editing. Further dialog boxes can be presented to assist in selection of parameter files or specifying a parameter file name for a new parameter file. Next, parameters can be edited, if appropriate. If a user specifies that a non-existing parameter file is to be loaded, an appropriate dialog box can be displayed advising that the parameter file does not exist. After clearing the message, the appropriate dialog box for specifying the parameter file can again be displayed, allowing correction of the error.

Figure 9:
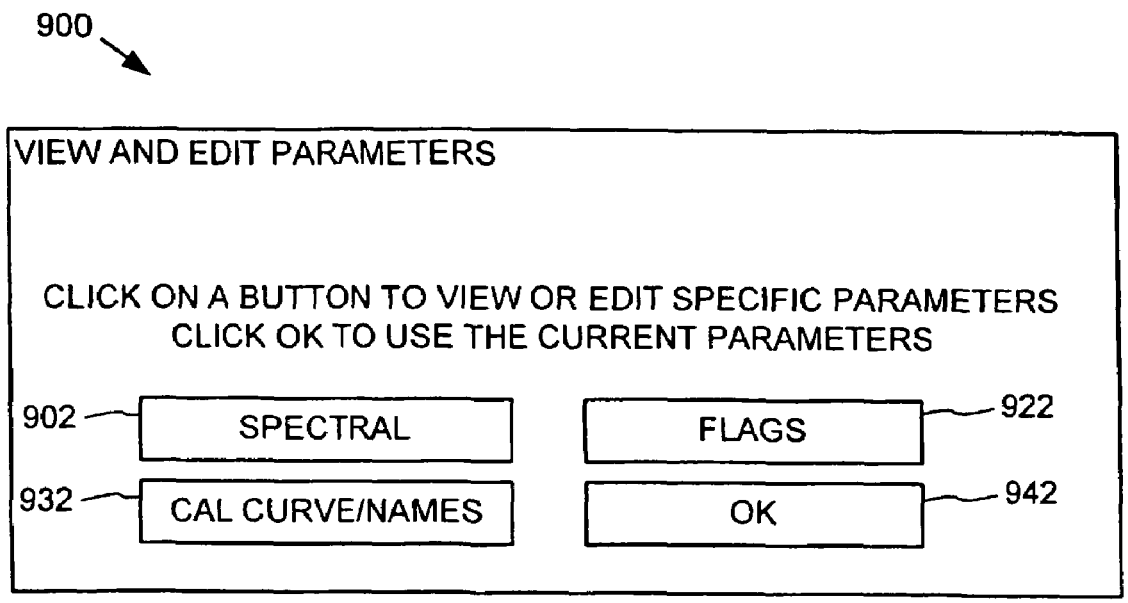
FIG. 9 is an exemplary graphical user interface for indicating which parameters are to be viewed or edited.

FIG. 9 shows an exemplary graphical user interface 900 for indicating which parameters are to be viewed for editing. If desired, the arrangement can be modified (e.g., Cal Curve and Names can be implemented as separate buttons and dialog boxes). Parameters can be grouped by family (e.g., according to parameter functionality).

A spectral analysis parameter family includes integration limits, peak positions, and interferent choice. A subfamily of the spectral analysis parameters includes choice of algorithms. A flags family includes parameters related to controlling suspect analysis warnings. A calibration curve family includes calibration parameters related to specifying mathematical calibration criteria, and a names family includes parameters for specifying names of analytes.

Upon activation of a user interface element (e.g., button) indicating a parameter family, parameters for the family are displayed in a parameter-editing graphical user interface by which a user can change the parameters.

For example, upon activation of the spectral user interface element 902, the user interface 1000 of FIG. 10 is displayed, by which the spectral analysis parameters (e.g., integration limits and peak positions) can be edited. If the parameters are acceptable to the user, the OK user interface element 1012 can be activated, and the user interface 900 of FIG. 9 can be displayed. Otherwise, the user can edit the displayed parameters via the parameter-editing graphical user interface 1000.

Figure 11A:
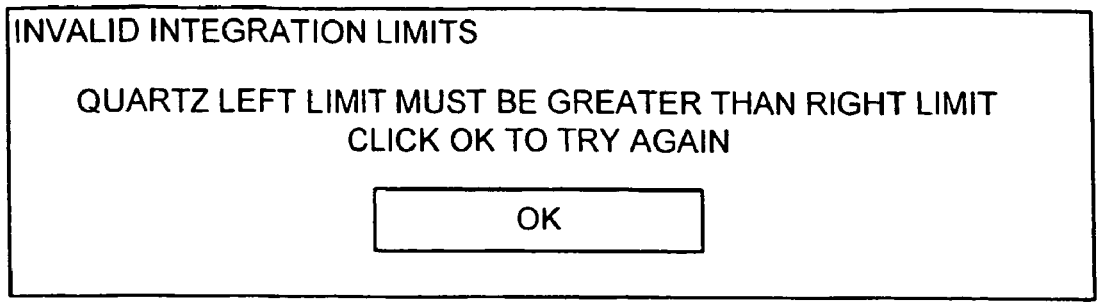
FIG. 11A is an exemplary suspect parameter condition advisory related to integration limits.
Figure 11B:
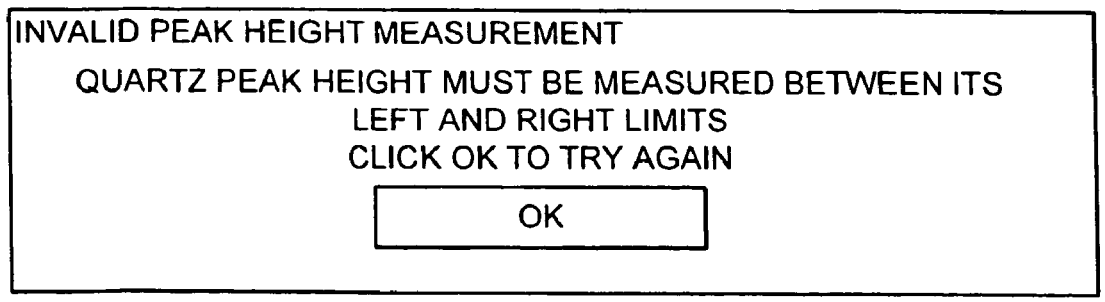
FIG. 11B is an exemplary suspect parameter condition advisory related to a peak position associated with integration limits.
Figure 11C:
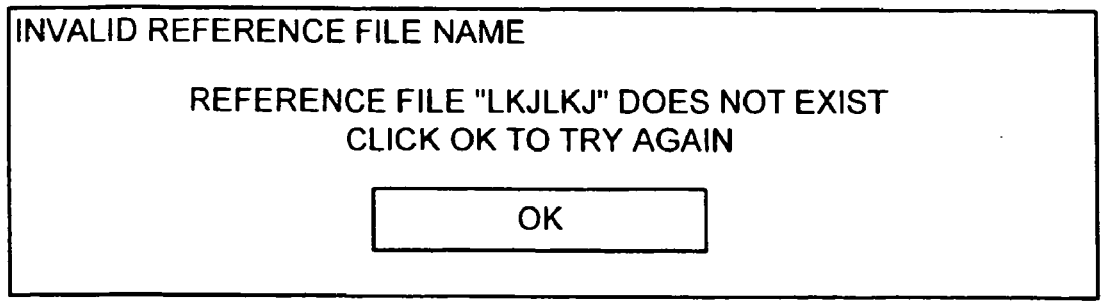
FIG. 11C is an exemplary suspect parameter condition advisory related to an invalid reference spectrum.

If the user enters integration limits in which a left limit is not greater than a right limit, a suspect parameter condition advisory 1100 such as that shown in FIG. 11A can be displayed by the software. If the user enters a peak position not between the right and left limits, a suspect parameter condition advisory 1130 such as that shown in FIG. 11B can be displayed. If an invalid reference spectrum (e.g., invalid file name) is specified by the user, a suspect parameter condition advisory 1160 such as shown in FIG. 11C can be displayed. The advisories can be displayed immediately upon entering the suspect parameter, or upon activation of the OK user interface element 1012. Immediately following display of the advisories, the user interface 1000 is again displayed by the software, giving the user an opportunity to edit the parameter and thus correct the suspect parameter condition.

The user interface element 1024 (FIG. 10) can be activated to display an appropriate dialog for choosing a different reference file.

Figure 12:
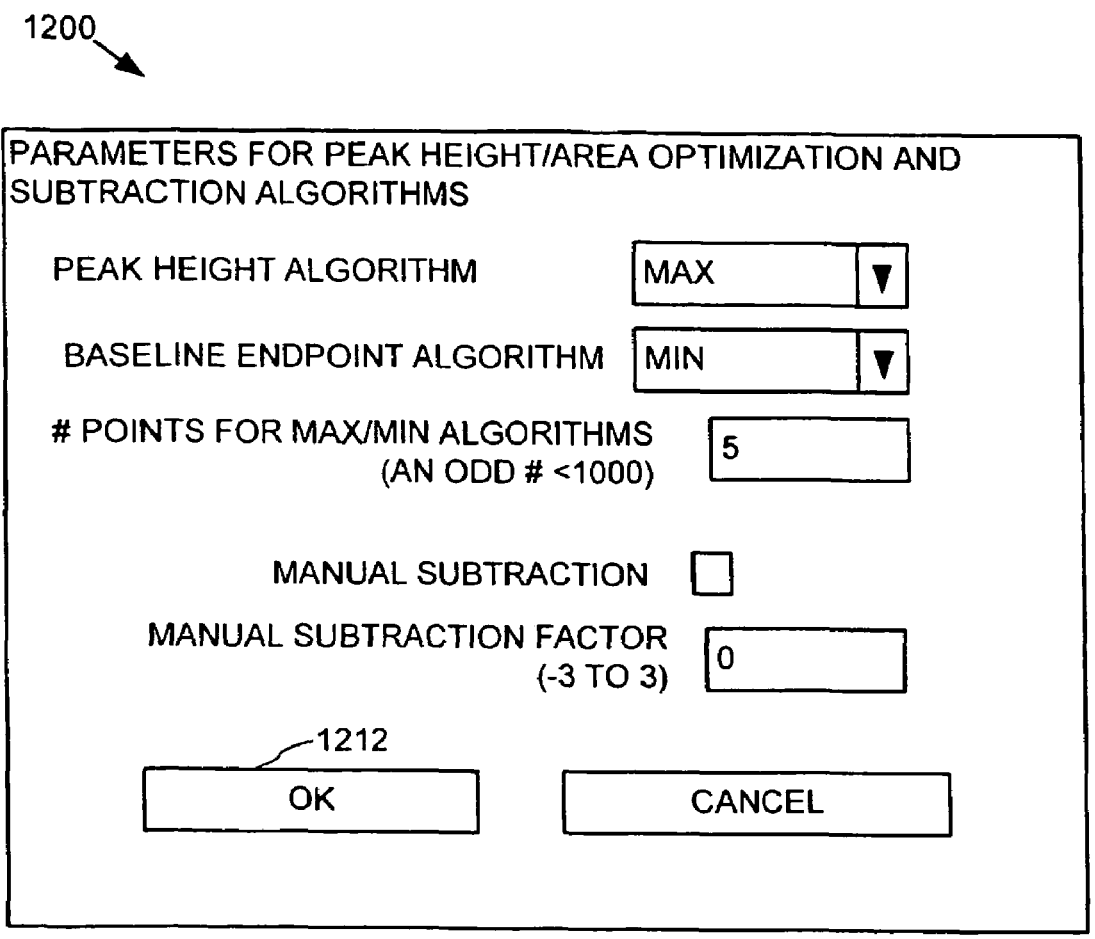
FIG. 12 is an exemplary user interface for viewing and editing various parameters.
Figure 13A:
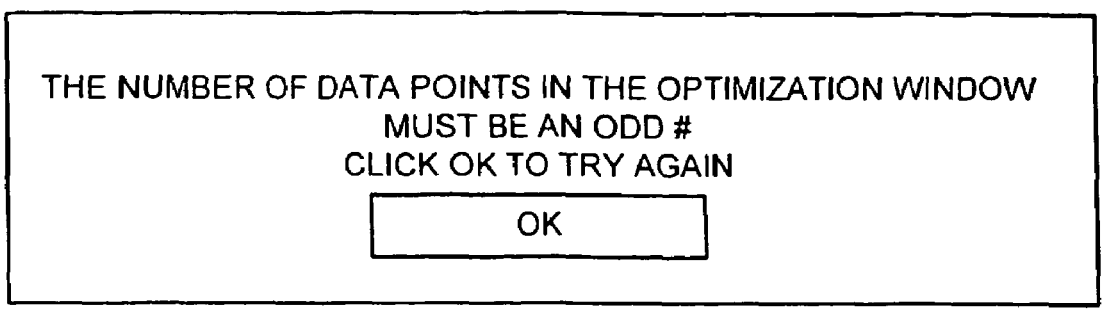
FIG. 13A is an exemplary suspect parameter advisory relating to an optimization window.

Upon activation of the user interface element 1032 for algorithms, the parameter-editing graphical user interface 1200 of FIG. 12 is presented. If the user enters a number of data points parameter that is not an odd number, the suspect parameter condition advisory 1300 of FIG. 13A is presented. Such an advisory can be displayed upon entry of the parameter or upon activation of the OK user interface element 1212 (FIG. 12). Responsive to dismissal of the advisory, the parameter-editing user interface 1200 of FIG. 12 is presented to give the user an opportunity to correct the condition.

Figure 13B:
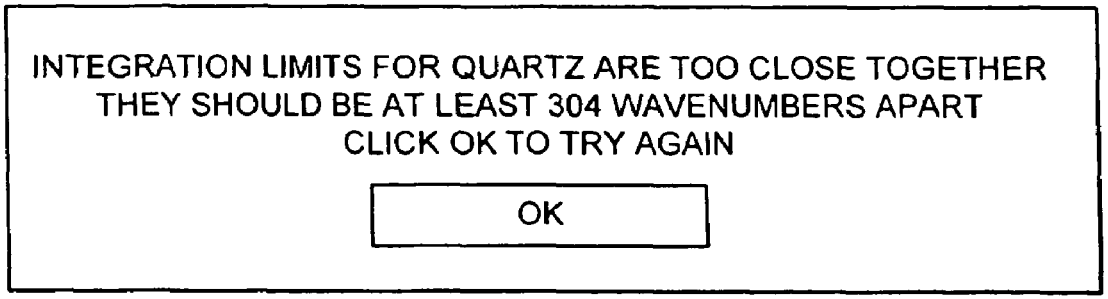
FIG. 13B is another exemplary suspect parameter advisory relating to an optimization window.

During automated analysis, if the integration limits for an analyte (e.g., quartz) are too close together (as determined in part by the number-of-points parameter), the suspect parameter condition advisory 1330 of FIG. 13B is presented. Upon dismissal of the advisory 1330, the parameter-editing graphical user interface 1000 (FIG. 10) is immediately displayed to give the user an opportunity to edit the integration limits and/or the number-of-points parameter in a subsequent graphical user interface 1200.

Returning now to FIG. 9, upon activation of the flags user interface element 922, the parameter-editing graphical user interface 1400 of FIG. 14 is presented by which a user can edit parameters controlling whether a suspect analysis condition is indicated in results.

Some of the parameters (e.g., quartz mass flag and negative peak area flag) are Boolean values and can be controlled by toggling a checkbox (e.g., checkbox 1412). Other parameters can be selected by choosing from picklists (e.g., the drop down list 1422, which shows a list of possible analytes indicating a region to measure signal).

Figure 15:
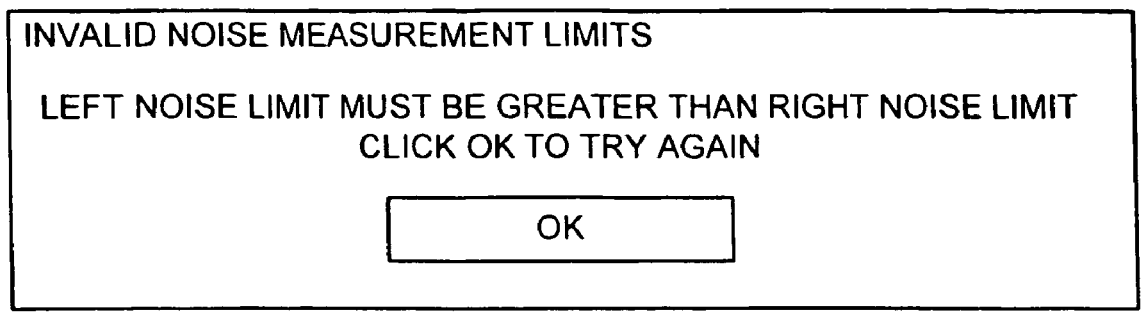
FIG. 15 is an exemplary suspect parameter condition advisory relating to signal-to-noise parameters.

If the left limit and right limit SNR parameters are in error (e.g., left limit is not greater than right limit), an advisory 1500 as shown in FIG. 15 is displayed. After the advisory, the software immediately displays the user interface 1400 of FIG. 14 to give the user an opportunity to correct the error.

Returning again to FIG. 9, upon activation of the cal curves/names user interface element 932, the parameter-editing graphical user interface 1600 of FIG. 16 is presented by the software. By the interface 1600, the user can edit calibration curve information and change the analyte names. Although quartz, kaolin, and limestone are shown, others (e.g., acetone) can be used.

Parameter Review

Upon completion of parameter editing (e.g., by activating the OK user interface element 942 of FIG. 9), a parameter review display 1700 of FIG. 17 is displayed. The user can then either return to changing the parameters or accept them via a user interface element to continue the automated analysis.

Calculations and Results

The automated analysis of the one or more selected spectra via a Fourier transform infrared spectroscopy technique then takes place according to the parameters. Various files can be generated and stored for subsequent analysis. For example, the results of spectrum subtraction (e.g., via a user-defined reference spectrum) can be stored (e.g., to persistent storage) with a file name related to the file name of the spectrum being analyzed (e.g., xST.SPC derived from the original spectrum x.SPC). A graphical user interface element can be provided to toggle off automatic saving of the subtraction spectra (e.g., to save storage capacity).

For automatic spectrum subtraction, a de-wiggle algorithm (e.g., such as the autosubtract algorithm available in the GRAMS/32 software) can be used. Such an approach can include minimizing the residual spectrum area in the first derivative of the subtraction result, using an iterative process. Alternatively, manual subtraction can be selected as described above.

After the subtraction result is available, the selected baseline endpoint and peak position optimization algorithms are applied. Baselines for the analyte peaks are drawn, and peak heights and areas are then calculated with respect to the baselines.

In a scenario having three analytes being quantified, the first analyte (e.g., analyte 1) can be regarded as the primary one and the other two as potential interferents or simply as secondary analytes. Calibration parameters are used to calculate the uncorrected analyte 1 mass, and corrected mass based on the impact of other analyte(s). The corrected analyte 1 mass is calculated by first applying the chosen absorbance correction, if any. If a strong peak of analyte 2 or 3 is being used to calculate a correction and there is only a shoulder or a secondary peak that overlaps with analyte 1, adjustments may need to be made (e.g., by a user) in how the interferent is measured and calibrated to prevent overcorrection of analyte 1.

In the example, the absorbance of analyte 1 is determined first, and then the interfering absorbance of either analyte 2 or 3 (as specified by the interferent parameter) may be subtracted from that of analyte 1 to obtain a corrected absorbance of analyte 1. The software can thus be used for automating the analysis of quartz mass on polymer membrane filters, including when other minerals are also present in the sample.

During analysis, various suspect analysis conditions (e.g., those based on signal-to-noise ratio, analyte mass, and negative peak area) can be detected. If detected, indication of the suspect analysis condition is provided with results of the analysis.

Upon completion, results are provided. In one implementation, the results are stored in a file having a name similar to the name of the file for the analyzed spectrum (e.g., in a file called x.DAT derived from the spectrum x.SPC). The length and content of the results can be dependent on the specific implementation, parameters utilized, as well as the analytical results for each sample. Exemplary results for one implementation are shown in Table 1.

TABLE 1

Exemplary Results

Data Analysis Report For Spectrum C:\WIN_IR\DATA\COAL\N25972TS.SPC
Date and Time Analysis Performed: Sep. 14, 2000 11:26
Parameter File Used = C:\WIN_IR\DATA\COAL\QUARTZ-PACK.PAR
Quartz Peak Height = .0995254
Quartz Peak Area = 1.04184
Kaolin Peak Height = .102127
Kaolin Peak Area = .937918
Limestone Peak Height = .0247229
Limestone Peak Area = .378525
Kaolin Correction = .102127
Limestone Correction = .0247229
Manual Subtraction is Off Manual Subtraction Factor = 0
Quartz Mass (uncorrected) = .0995254
Quartz Mass (corrected) = .0995254
Interferent Correction Used = None
Results of Quartz Mass Flag: In Linear Quartz Mass Range
Quartz Mass Limits are from 0 to 5000
Quartz Region SNR = 1.34446
Kaolin Region SNR = 1.3796
Limestone Region SNR = .333974
Lowest Allowed SNR = 3
FAILED SNR Test in Quartz Region
Noise Measurement Region is From 640 To 600 Noise Level = .0740263
Quartz Peak Area is Positive
Kaolin Peak Area is Positive
Limestone Peak Area is Positive
Negative Peak Area Flag is On Negative Peak Area Limit = 1 Percent
Quartz Negative Peak Area of .00357901 Percent is Less Than the Allowed Limit
Kaolin Negative Peak Area of 0 Percent is Less Than the Allowed Limit
Limestone Negative Peak Area of 0 Percent is Less Than the Allowed Limit
PVC Reference spectrum = C:\WIN_IR\PVC2MAY9.SPC
Quartz Integration Parameters
Fixed Parameters: Left X = 815 Right X = 770 Peak Top = 800
Using Peak Height Algorithm = Max and Baseline Endpoint Algorithm = Min
Left X = 819.745 Right X = 769.596 Peak Top = 800.457
Kaolin Integration Parameters

TABLE 1-continued

Exemplary Results

Fixed Parameters: Left X = 950 Right X = 900 Peak Top = 917
Using Peak Height Algorithm = Max and Baseline Endpoint
Algorithm = Min
Left X = 948.975 Right X = 896.897 Peak Top = 914.256
Limestone Integration Parameters
Fixed Parameters: Left X = 895 Right X = 840 Peak Top = 877
Using Peak Height Algorithm = Max and Baseline Endpoint
Algorithm = Min
Left X = 896.897 Right X = 844.819 Peak Top = 873.751
Optimization Window = 5 Data points
Calibration Curve Info
Quartz Cal. Curve: Slope = 1 Y intercept = 0
Kaolin Cal. Curve: Slope = 1 Y intercept = 0
Limestone Cal. Curve: Slope = 1 Y intercept = 0

Various suspect analysis warnings (e.g., "FAILED SNR Test") are provided with the results, as appropriate, to indicate that various aspects of the analysis are suspect.

Parameter File Format

Any number of formats can be used to store the parameters. The length and content of parameter lists can be dependent on the specific implementation and the parameters utilized. An exemplary format in ASCII text is shown in Table 2. In the example, parameters are recognized by virtue of their position within the file. The file can be edited with any text editor, or more easily by the parameter-editing capabilities provided by the described software.

TABLE 2

Exemplary Parameter File Format

| Value | Explanation (need not be stored in file) |
|---|---|
| C:\WIN_IR\PVC2MAY9.SPC | Name of reference spectrum (e.g., PVC) |
| 1 | Peak position algorithm: 0 = None, 1 = Max, 2 = Center of Mass |
| 1 | Baseline endpoint algorithm: 0 = None, 1 = Min, 2 = Find Peak |
| 5 | No. of data points (odd) in optimization window |
| 815 | Analyte #1 left baseline endpoint |
| 770 | Analyte #1 right baseline endpoint |
| 800 | Position of Analyte #1 peak height measurement (e.g., peak position) |
| 950 | Analyte #2 left baseline endpoint |
| 900 | Analyte #2 right baseline endpoint |
| 917 | Position of Analyte #2 peak height measurement (e.g., peak position) |
| 895 | Analyte #3 left baseline endpoint |
| 840 | Analyte #3 right baseline endpoint |
| 877 | Position of Analyte #3 peak height measurement (e.g., peak position) |
| 1 | Analyte #1 calibration curve slope |
| 0 | Analyte #1 calibration curve Y-intercept |
| 1 | Analyte #2 calibration curve slope |
| 0 | Analyte #2 calibration curve Y-intercept |
| 1 | Analyte #3 calibration curve slope |
| 0 | Analyte #3 calibration curve Y-intercept |
| 640 | Left wavenumber of noise measurement region |
| 600 | Right wavenumber of noise measurement region |
| 1 | Region for SNR flag: 0/1/2/3 = None/Analyte 1/Analyte 2/Analyte 3 |
| 3 | Lowest allowable SNR |
| 1 | Analyte 1 mass flag: 0 = No, 1 = Yes |
| 0 | Lower analyte 1 mass limit |
| 5000 | Upper analyte 1 mass limit |
| Quartz | Name of analyte 1 |
| Kaolin | Name of analyte 2 |

TABLE 2-continued

Exemplary Parameter File Format

| Value | Explanation (need not be stored in file) |
|---|---|
| Limestone | Name of analyte 3 |
| 1 | Negative peak area flag: 0 = Off, 1 = On |
| 1 | Percent negative peak area allowed |
| 0 | Manual subtraction: 0 = Off, 1 = On |
| 0 | Manual subtraction factor |
| 0 | Choose interferent correction: 0 = None, 1 = Analyte 2, 2 = Analyte 3 |

Exemplary Enhancement Relating to Internal Standard

If desired, quantification of analytes, which can include interferents, can be accomplished with respect to a standard material in a standard quantity. For example, an internal standard can be utilized whereby a known quantity of a reference analyte is introduced into a sample.

In such a scenario, a spectral ratio between known quantities of the analyte and reference material can be first determined. Given the ratio, a ratio factor can be used to calculate the quantification metric (e.g., mass or concentration) for the analyte when of unknown quantity in samples (e.g., based on the known quantity of the reference analyte). In any of the examples described herein, such an approach can be applied. Appropriate adjustments to the user interfaces, parameters stored, and output can be made. For example, a user interface can be constructed or modified to accept a ratio factor. If desired, the ratio factor parameter can be implemented by storing and displaying as the parameter(s) related to calibration curve slope.

Exemplary Enhancement Regarding Analytes and Interferents

Although some of the examples herein describe scenarios involving a primary analyte and two associated analytes that can selectively be considered as interferents, alternative scenarios are possible. For example, the software can support a scenario involving one or more analytes with respective associated interferent analytes. In such scenarios, to prevent confusion on the part of the user, the interferent analytes can simply be presented as "interferents" in user interfaces and output reports. However, calculations and functionality that treat the interferent as an analyte can be performed for the interferents.

For example, a pairing scenario can be supported. In such a scenario, any number of analytes can be quantified, with respective paired interferents (e.g., each analyte having a paired interferent). In one implementation, three analytes, each with an associated interferent can be used.

When performing quantification calculations relating to analytes, the appropriate interferent (e.g., the one paired with an analyte) can be used. In this way, quantification for a plurality of analytes (e.g., each having an interferent) can be accomplished.

If desired, quantification calculations can also be performed for the interferents. Results of such calculations (e.g., the mass or concentration of an interferent) can be shown in output.

Appropriate adjustments to the user interfaces (e.g., additional or different user interface elements), parameters, and output can be made accordingly. FIG. 18 shows an exemplary user interface 1800 by which analyte names can be viewed and edited (e.g., by entering into an edit box 1822). Such a user interface 1800 can be used as an alternative to the user interface 1600 of FIG. 16. Some of the analytes are called "interferents" to indicate that they are paired with particular analytes and used in interferent correction analyses for the respective analyte.

In the example, an internal standard name can be viewed and edited (e.g., via the edit box 1842). If a standard name is specified (e.g., there is text in the edit box 1842), the software will take appropriate steps with respect to the internal standard (e.g., with reference to a ratio factor). Otherwise (e.g., the edit box 1842 is empty), calculations for the internal standard are not performed.

Further, FIG. 19 shows an alternative exemplary user interface 1900 that can be used as an alternative to the user interface 1000 shown in FIG. 10. In the example, pairs of analytes (e.g., quartz and kaolin) are considered to be an analyte and a respective interferent for the analyte. Although only one pair is shown, an additional number of pairs can be supported. In various implementations, it may not be desirable or necessary to implement a user interface element (e.g., a pick list) for choosing between analytes to serve as interferents (e.g., such as that shown as "Interferent Choice" in FIG. 10). If desired, a box by which a reference file name can be specified can be added to the interface 1900.

Parameters related to an internal standard are shown at 1920. The buttons 1912, 1924, and 1932 can function similarly to the buttons 1012, 1024, and 1032, respectively, of FIG. 10.

Further, appropriate changes can be made in the exemplary user interface 1400 of FIG. 14. For example, the drop down list 1422 can be removed. Additional parameters for analyte quantity (e.g., absorbance or mass) flag, lower limit, and upper limit can be included in the user interface 1400 for respective analytes. If desired, such parameters for the respective analytes can be collected via another user interface (e.g., a separate window). In an example using pairing, parameters for six analytes (e.g., three "analytes" and three "interferents") can be shown, stored, and output. However, any other number can be implemented.

Exemplary Quantification Alternatives

Although some of the examples herein describe quantification in terms of mass, in any of the technologies described herein, the software can be alternatively implemented so that some other quantification metric can be used. Exemplary quantification metrics include concentration (e.g., percentage, grams/liter, milligrams/deciliter, pounds/cubic foot, mole/liter, and the like), any metric indicating mass (e.g., milligrams, micrograms, and the like), as well as any other units of measure.

In any of the user interfaces, parameters, and output described herein, appropriate changes can be made accordingly. For example, a user interface can be presented whereby a user selects the desired metric. FIG. 20 shows an exemplary user interface 2000 including a field 2012 for specifying analyte quantification units. A parameter tracking the metric can store the desired metric. Further, output can include an indication of the metric.

Also, adjustments relating to suspect analysis conditions can be made. For example, rather than having a flag based on mass, lower and upper limits of any arbitrary concentration can be specified (e.g., for each analyte, including interferents). Corresponding adjustments to the user interface, parameters, and output can be made. The flags can also be responsive of absorbance.

Exemplary Enhancement Regarding Absent Parameter Detection

In any of the examples described herein, the software can support absent parameter detection. For example, in the case of a user interface, a user may opt to simply leave a user interface element (e.g., a field) blank. Responsive to detecting that a field is blank, the software can take appropriate steps (e.g., via a Boolean branching statement).

For example, if a field related to a manual subtraction factor is presented, a user may simply leave the field blank. When the user interface is completed (e.g., by clicking on an appropriate "OK" button), the software can take appropriate steps (e.g., not perform manual subtraction).

In another example, a user may leave a field for an analyte name blank. If left blank, the software can then take appropriate steps (e.g., not present editable parameters for the blank analyte, not perform calculations for the blank analyte, or both). The presence of an analyte name causes the software to expect to see related data. If not completed, an appropriate error message or other condition can be triggered.

Finally, the absence of a parameter can be used to control the value of any Boolean parameter. For example, if the parameter is present, an associated Boolean parameter can be set to true. If the parameter is absent, the parameter can be set to false, or vice versa.

Exemplary Other Enhancements

In certain embodiments, it may be desirable to allow a user to choose calibration type (e.g., choose between peak height and peak area). However, if peak area is chosen, peak height may still be calculated for signal-to-noise (e.g., signal-to-noise ratio) purposes. FIG. 20 includes a drop down list 2022 by which a user can selectively specify whether peak height or peak area is desired. An additional parameter can be collected and stored accordingly.

If desired, various of the features can be omitted or modified. For example, suspect parameter or analysis conditions can be omitted or their conditions softened.

Similarly, the ranges for calibration parameters (e.g., calibration curve slope and calibration curve y intercept as shown in FIG. 16) can be eliminated altogether or softened (e.g., the ranges expanded) to enable greater flexibility in the software. Accordingly, any values can be accepted without triggering a suspect parameter condition. Such an arrangement can facilitate quantification for a wider variety of analytes and in a wider variety of analytical procedures.

In another example, the integration limit range between 4000 and 150 cm$^{-1}$ can be modified to any number of alternatives (e.g., 40000 and 10 cm$^{-1}$). Similarly, the manual subtraction factor range −3 to +3 can be modified to any number of alternatives (e.g., −5 to +5). Any such ranges can be used to trigger suspect parameter or analysis conditions.

Further, the region-to-measure-signal parameter indicating the signal portion to be used for signal-to-noise calculations can be omitted. For example, signal-to-noise ratio can be measured for more than one analyte (e.g., with reference to peak height for the respective analyte).

Still further, a feature related to automatic subtraction can be supported as shown in the user interface 2100 of FIG. 21.

The parameters 2110 can be used to manipulate such a feature instead of adjusting the program code. The button 2112 can function similarly to the button 1212 of FIG. 12.

Figure 22:
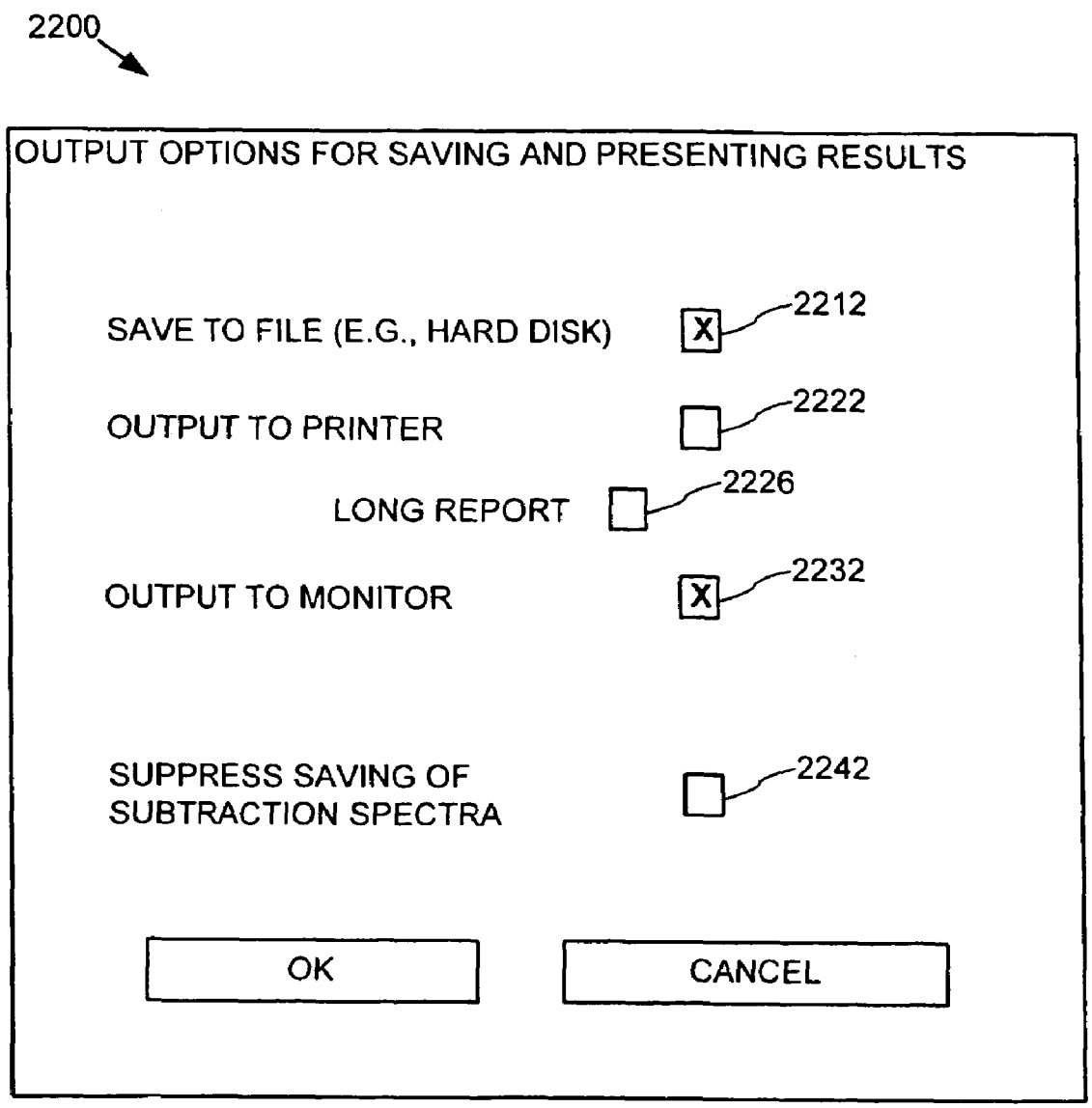
FIG. 22 is an exemplary user interface for viewing and editing parameters related to saving and presenting results.

If desired, additional parameters (e.g., in an output parameter family) can be added for output options. For example, a user can designate whether output will go to the display, a file (e.g., on a hard disk), a printer, or some combination thereof. Appropriate adjustments to the user interface (e.g., via addition of user interface elements, such as checkboxes or the like), addition of parameters, and changes to the output can be made. Further, the software can present various levels of reports (e.g., full report, intermediate report, or summary report). Also, a parameter can be specified to suppress saving of subtraction results. Such parameters can be controlled via an exemplary user interface 2200 shown in FIG. 22. The checkboxes 2212, 2222, 2226, 2232, and 2242 can be manipulated to control their respective functionality.

Exemplary Alternative Output Indicating Parameters for Review

Table 3 shows an exemplary alternative format and content for providing output indicating values being used for parameters. Such an arrangement can be used in place of the parameter review display 1700 of FIG. 17. The length and content of the review display can be dependent on the specific implementation utilized, as well as analytical choice for analysis of the samples.

TABLE 3

Exemplary Parameter Review Display

Integration Limits for Quartz
Left X = 815 Right X = 770 Peak height measured at 800
Integration Limits for [Interferent 1]
[Additional information can be here for other analytes/interferents]
Peak Height Algorithm = Max Baseline Endpoint Algorithm = Min
Optimization Window = 3 Data points
Reference spectrum = None
Automatic Subtraction is Off
The Auto. Sub. Left Optimization Limit = 0
The Auto. Sub. Right Optimization Limit = 0
Manual Subtraction is Off Manual Subtraction Factor = 0
Flagging Parameters
Noise measured from 2200 to 2000
Lowest Allowed SNR = 0
Quartz Mass Flag is Off
Quartz Mass Limits are from 0 to 0
Negative Peak Area Flag is Off
Negative Peak Area Limit = 0 Percent
Calibration Curve Info.
Quartz Cal. Curve: Slope = 1 Y Intercept = 0
[Interferent 1] Cal. Curve: Slope = 0 Y intercept = 0 Peak Ratio = 0
[Additional information can be here for other Analytes and Interferents]
Analyte Prediction Units = Moles/Liter
Calibration Type = Peak Height
[Can also include graphical buttons similar to those of FIG. 17]
[For clarification, the "OK" button can be implemented as a "Begin Analysis" button]

Exemplary Use of Calibration

In one example, there can be two types of calibration methods, the use of which can be determined by whether matrix effects in the analysis are strong or inconsequential. A sample "matrix" can specify the sample's overall nature, character, and composition. The matrix can describe the material situation in which an analyte is found. A "matrix effect" can specify influence on the results of an analysis, which can indicate either more or less analyte than is actually present, caused by the nature of the sample inhibiting or enhancing the response of the sample to the analytical procedure.

When matrix effects are absent, a series of pure analyte calibration standards are prepared in the laboratory, their absorbance response is measured, and the results can be used to enter a calibration line slope in the analytical software. The same can be done for respective interferents, if any. In this mode of practice, the calibrations for both analyte and interferent are based on pure materials.

However, if matrix effects are known to be significant, the calibration standards for the analyte are prepared to contain varying ratios of mixed analyte and interferent. When absorbance response is measured, and the results used to enter a calibration line slope in the software, the entered calibration will somewhat reflect the known matrix effect, helping to correct for the phenomenon. In these circumstances, an additional calibration based on pure interferent standards can also be prepared to apply further correction for its presence in the sample.

Alternatives

Although the above examples describe Fourier transform infrared spectroscopy ("FTIR"), the techniques can be equally applied to other infrared spectroscopy techniques involving digitized infrared spectra as may have been derived from any infrared spectroscopic technique or method employed by an analyst. Infrared techniques can include analyses ranging from 15–15,000 wavenumbers or approximately 15–15,000 wavenumbers (e.g., near-, mid-, and far-infrared). Further, any of the technologies (e.g., parameters and the user interfaces) can be applied to other spectroscopy. For example, the technologies can be applied to Raman spectroscopy, UV-visible ("UV-vis") spectroscopy, nuclear magnetic resonance ("NMR") spectroscopy, electron paramagnetic resonance ("EPR" or "ESR") spectroscopy, x-ray diffraction ("XRD") spectroscopy, or other spectroscopy techniques. A range of 10–40,000 wavenumbers or approximately 10–40,000 wavenumbers can be used to accommodate analysis for infrared, UN-vis, and Raman spectroscopy.

Although some of the above examples describe particular user interface arrangements, any number of alternative user interface arrangements can be used in conjunction with the technologies. For example, additional, fewer, or different user interface elements (e.g., checkboxes, fields, windows, and the like) can be used in any number of alternatives to achieve similar functionality. Further, respective changes can be made by adding, removing, or changing parameters (e.g., in a parameter file), and output results (e.g., shown in an output report).

For any of the methods described herein, the actions can be performed by computer-executable instructions stored in one or more computer-readable media. Such actions can be performed automatically or semi-automatically (e.g., with or without user input).

In view of the many possible embodiments to which the principles of the invention may be applied, it should be recognized that the illustrated embodiments are examples of the invention, and should not be taken as a limitation on the scope of the invention. Rather, the scope of the invention includes what is covered by the following claims. We therefore claim as our invention all that comes within the scope and spirit of these claims.

We claim:

1. A computer-implemented method for measuring a quantity of one or more analytes in a sample via Fourier transform infrared spectroscopy, the computer-implemented method comprising:
    presenting one or more parameter-editing user interfaces depicting a set of a plurality of parameters controlling spectral analysis of a digitized version of a spectrum acquired for the sample via Fourier transform infrared spectroscopy and indications of the parameters' functionality, the set of the plurality of parameters comprising at least one core absorbance band parameter for at least one analyte;
    acquiring from user input, via the one or more parameter-editing user interfaces, values for one or more parameters out of the set of the plurality of parameters;
    detecting a suspect parameter condition in the one or more parameters;
    responsive to detecting the suspect parameter condition, displaying an advisory indicating the suspect parameter condition; and
    performing an automated quantitative spectral analysis of the digitized version of the spectrum via a Fourier transform infrared spectroscopy technique as indicated by the set of the plurality of parameters.

2. The computer-implemented method of claim 1 wherein the set of the plurality of parameters comprises parameters for calibration of the automated quantitative spectral analysis, wherein at least one of the parameters for calibration selects between peak height and peak area quantitation of analytes.

3. The computer-implemented method of claim 1 wherein the automated quantitative spectral analysis comprises applying a calibration-related ratio factor based on a known quantity of a reference analyte in the sample.

4. The computer-implemented method of claim 1 wherein the set of the plurality of parameters comprises a parameter operable to select a center of mass algorithm for finding a peak height for an analyte.

5. The computer-implemented method of claim 1 wherein the set of the plurality of parameters comprises parameters for indicating the names of one or more analytes to be detected during the automated quantitative spectral analysis.

6. The computer-implemented method of claim 1 wherein at least one of the analytes is quartz.

7. The computer-implemented method of claim 1 further comprising:
    after displaying the advisory, displaying at least one of the parameter-editing user interfaces displaying at least one parameter related to the suspect parameter condition, wherein the at least one parameter related to the suspect parameter condition can be edited via the one or more parameter-editing user interfaces.

8. The computer-implemented method of claim 7 wherein the suspect parameter condition relates to at least one core absorbance band parameter for at least one of the analytes;
    the detecting detects a suspect parameter condition related to the at least one core absorbance band parameter;
    displaying an advisory comprises displaying an advisory indicating the suspect parameter condition related to the at least one core absorbance band parameter; and
    displaying at least one of the parameter-editing user interfaces comprises displaying at least one parameter related to the suspect parameter condition in the at least one core absorbance band parameter, wherein the at least one core absorbance band parameter related to the suspect parameter condition can be edited via the one or more parameter-editing user interfaces.

9. The computer-implemented method of claim 8 wherein the suspect parameter condition comprises an impossible peak position for the at least one analyte.

10. The computer-implemented method of claim 8 wherein the suspect parameter condition comprises an impossible integration limit for the at least one analyte.

11. The computer-implemented method of claim 1 wherein
    the set of the plurality of parameters controlling spectral analysis comprises at least one parameter indicating an interferent for which correction is to be applied during the automated quantitative spectral analysis; and
    the analysis applies correction for the indicated interferent.

12. The computer-implemented method of claim 1 wherein the set of the plurality of parameters controlling spectral analysis comprises at least one parameter indicating a baseline endpoints algorithm to be applied during the automated quantitative spectral analysis; and
    the analysis applies the baseline endpoints algorithm indicated.

13. The computer-implemented method of claim 12 wherein the set of the plurality of parameters further comprises a number-of-points parameter indicating a window for use with the baseline endpoints algorithm.

14. The computer-implemented method of claim 13 wherein the set of the plurality of parameters controlling spectral analysis comprises at least one parameter indicating one or more peak height algorithms to be applied during the automated quantitative spectral analysis;
    the analysis applies the one or more peak height algorithms indicated; and
    a number-of-points parameter indicates a window also for use with the one or more peak height algorithms.

15. The computer-implemented method of claim 13 further comprising:
    after displaying the advisory, displaying one or more parameter-editing user interfaces displaying at least one parameter related to the suspect parameter condition, wherein the parameter related to the suspect parameter condition can be edited via the one or more parameter-editing user interfaces, wherein the suspect parameter condition comprises that the number-of-points parameter has an even value or is within a given range.

16. The computer-implemented method of claim 1 wherein
    the set of the plurality of parameters controlling spectral analysis comprises at least one parameter indicating a baseline endpoint algorithm to be applied during the automated quantitative spectral analysis; and
    the analysis applies the baseline endpoint algorithm indicated.

17. The computer-implemented method of claim 1 wherein the one or more parameters are grouped for display among a plurality of the parameter-editing user interfaces based on functionality of the parameters.

18. The computer-implemented method of claim 1 wherein the automated quantitative spectral analysis comprises:
    automatically subtracting a reference spectrum specified by at least one of the parameters to generate a subtraction spectrum; and
    automatically saving the subtraction spectrum to persistent storage.

19. The computer-implemented method of claim 18 further comprising:
receiving an indication via a graphical user interface element that automatic saving is to be inhibited; and
responsive to receiving the indication, inhibiting automatic saving.

20. The computer-implemented method of claim 1 wherein the presenting comprises:
presenting parameters for a plurality of pairs of two analytes, wherein a first of two analytes is presented as an analyte and a second of the two analytes is presented as an interferent associated with the first of the two analytes; and
wherein the automated quantitative spectral analysis comprises an interferent correction calculation for the first analyte based on parameters associated with the second analyte.

21. The computer-implemented method of claim 1 further comprising:
detecting that a user interface element related to at least one of the parameters has not been completed; and
responsive to detecting that the user interface element has not been completed, omitting to perform processing related to the user interface element.

22. The computer-implemented method of claim 1 wherein:
the set of the plurality of parameters comprises a units-of-measurement parameter indicating units for a quantification metric generated during the automated quantitative spectral analysis.

23. The computer-implemented method of claim 1 wherein the set of the plurality of parameters comprises a data output indicator.

24. The computer-implemented method of claim 1, further comprising:
during automated quantitative spectral analysis, detecting whether one or more suspect analysis conditions are present; and
if one or more suspect analysis conditions are not detected to be present, displaying an advisory accordingly.

25. A computer-readable storage medium comprising computer-executable instructions for performing a computer-implemented method for measuring the quantity of one or more analytes in a sample via Fourier transform infrared spectroscopy, the computer-implemented method comprising:
presenting one or more parameter-editing user interfaces depicting a set of a plurality of parameters controlling spectral analysis of a digitized version of a spectrum acquired for the sample via Fourier transform infrared spectroscopy and indications of the parameters' functionality, the set of the plurality of parameters comprising at least one core absorbance band parameter for at least one analyte;
acquiring from user input, via the one or more parameter-editing user interfaces, values for one or more parameters out of the set of the plurality of parameters;
detecting a suspect parameter condition in the parameters;
responsive to detecting the suspect parameter condition, displaying an advisory indicating the suspect parameter condition; and
performing an automated quantitative spectral analysis of the digitized version of the spectrum via a Fourier transform infrared spectroscopy technique as indicated by the set of the plurality of parameters.

26. A computer-implemented method for measuring a quantity of one or more analytes in a sample via Fourier transform infrared spectroscopy, the computer-implemented method comprising:
presenting one or more parameter-editing user interfaces depicting a set of a plurality of parameters controlling spectral analysis of a digitized version of a spectrum acquired for the sample via Fourier transform infrared spectroscopy and indications of the parameters' functionality, the set of the plurality of parameters comprising at least one core absorbance band parameter for at least one analyte;
acquiring from user input, via the one or more parameter-editing user interfaces, values for one or more parameters out of the set of the plurality of parameters;
performing an automated quantitative spectral analysis of the digitized version of the spectrum via a Fourier transform infrared spectroscopy technique as indicated by the set of the plurality of parameters;
acquiring from user input, values for one or more suspect analysis condition detection parameters, wherein, during the quantitative spectral analysis, one or more suspect analysis conditions are detected according to the parameters; and
providing results of the automated quantitative spectral analysis, wherein the results include an indication that one or more suspect analysis conditions were detected.

27. The computer-implemented method of claim 26 wherein
the one or more suspect analysis condition detection parameters include at least one parameter related to a signal-to-noise ratio test; and
the indication comprises an indication that the spectrum failed the signal-to-noise ratio test.

28. The computer-implemented method of claim 27 wherein the parameter related to a signal-to-noise ratio test comprises a wavenumber boundary for a measurement region for the signal-to-noise ratio test.

29. The computer-implemented method of claim 26 wherein
the one or more suspect analysis condition detection parameters include at least one parameter related to an analyte quantity test; and
the indication comprises an indication that the spectrum failed the analyte quantity test.

30. The computer-implemented method of claim 26 wherein
the one or more suspect analysis condition detection parameters include at least one parameter related to an absorbance range test; and
the indication comprises an indication that the spectrum failed the absorbance range test.

31. The computer-implemented method of claim 26 wherein
the one or more suspect analysis condition detection parameters include at least one parameter related to a negative peak area test; and
the indication comprises an indication that the spectrum failed the negative peak area test.

32. The computer-implemented method of claim 26 wherein a Boolean parameter controls whether the one or more suspect analysis conditions are monitored, and the Boolean parameter is modifiable by a user via at least one of the parameter-editing user interfaces, wherein the one or more parameter-editing user interfaces comprises a graphical user interface.

33. A computer-implemented method for measuring a quantity of an analyte in a sample via Fourier transform infrared spectroscopy, the computer-implemented method comprising:

presenting one or more parameter-editing user interfaces depicting a set of parameters controlling spectral analysis of a digitized version of a spectrum acquired for the sample via Fourier transform infrared spectroscopy and indications of the parameters' functionality, the set of parameters comprising integration limits and peak position for at least the analyte, indication of an interferent for use during an interferent correction technique, choice of a peak height algorithm, choice of a baseline endpoint algorithm, a number-of-points parameter, a manual subtraction factor, and calibration curve parameters;

acquiring from user input, via the one or more parameter-editing user interfaces, values for one or more parameters out of the set of parameters; and performing an automated quantitative spectral analysis of the digitized version of the spectrum via a Fourier transform infrared spectroscopy technique as indicated by the set of parameters.

34. The computer-implemented method of claim 33 further comprising:

acquiring via the one or more parameter-editing user interfaces, values for one or more suspect analysis condition detection parameters, wherein, during the quantitative spectral analysis, one or more suspect analysis conditions are detected according to the set of parameters; and providing results of the automated quantitative spectral analysis, wherein the results include an indication that the one or more suspect analysis conditions were detected, wherein the one or more suspect analysis condition detection parameters comprise parameters for performing a signal-to-noise ratio test, an analyte absorbance test, and a negative peak area test.

35. A computer-implemented method for measuring a quantity of a plurality of analytes in a sample via Fourier transform digital spectroscopy, the computer-implemented method comprising:

presenting one or more parameter-editing user interfaces depicting a set of parameters controlling spectral analysis of a digitized version of a spectrum acquired for the sample via Fourier transform spectroscopy and indications of the parameters' functionality, the set of parameters comprising integration limits and peak position for the analytes, indication of respective interferents paired with the analytes for use during an interferent correction technique, choice of a peak height algorithm, choice of a baseline endpoint algorithm, a number-of-points parameter, an indication of whether saving of subtraction spectra is to be suppressed, and calibration curve parameters;

acquiring from user input, via the one or more parameter-editing user interfaces, values for one or more parameters out of the set of parameters; and performing an automated quantitative spectral analysis of the digitized version of the spectrum via a Fourier transform spectroscopy technique as indicated by the set of parameters.

36. A computer-implemented method for measuring a quantity of an analyte in a sample, the method comprising:

acquiring from user input, via a parameter-editing graphical user interface, a set of parameters controlling analysis of digitized spectral data acquired for the sample, the set of parameters comprising core absorbance band parameters for at least the analyte;

detecting a suspect parameter condition related to the core absorbance band parameters;

displaying an advisory indicating the suspect parameter condition in the core absorbance band parameters; and after displaying the advisory, displaying a parameter-editing graphical user interface displaying at least one parameter related to the suspect parameter condition in the core absorbance band parameters, wherein the parameter related to the suspect parameter condition can be edited.

37. The computer-implemented method of claim 36, wherein the set of parameters further comprises:

editable parameter values indicating a left limit and a right limit for measuring noise for a signal-to-noise ratio test; and an editable parameter value indicating a lowest allowable signal-to-noise ratio permitted by the signal-to-noise ratio test.

38. The computer-implemented method of claim 36, wherein the set of parameters further comprises an indicator whether a suspect analysis condition should be monitored.

39. The computer-implemented method of claim 36, wherein the set of parameters further comprises a data output indicator.

40. A computer-implemented method of analyzing a digitized version of a spectrum to quantify an amount of quartz in a sample, wherein the digitized version of the spectrum comprises a representation of a spectral analysis of the sample, the method comprising:

acquiring via a graphical user interface, a set of parameters, wherein the set of parameters comprises one or more suspect analysis condition parameters for identifying a suspect analysis condition in the digitized version of the spectrum and one or more parameters to control analysis of the digitized version of the spectrum;

analyzing the digitized version of the spectrum via the parameters; and outputting results of analyzing the digitized version of the spectrum, wherein the results comprise an indication of the amount of quartz in the sample and an indication of the suspect analysis condition in the spectrum based on the one or more suspect analysis condition parameters input by the user via the graphical user interface.

41. A computer-implemented method of obtaining parameters to analyze a digitized version of a spectrum to quantify an amount of quartz in a sample, wherein the digitized version of the spectrum comprises a representation of a spectral analysis of the sample, the method comprising:

acquiring via a graphical user interface, a set of one or more parameters controlling analysis of the digitized version of the spectrum;

detecting a suspect condition in the set of one or more parameters controlling analysis of the digitized version of the spectrum;

responsive to detecting the suspect condition, generating an advisory graphical user interface indication of the suspect parameter condition in the set of one or more parameters controlling analysis of the digitized version of the spectrum; and after presenting the advisory graphical user interface indication, presenting a graphical user interface displaying one or more parameters related to the suspect condition, wherein the graphical user interface permits editing of the one or more parameters related to the suspect condition.

42. An automated system for performing automated quantitative analysis of a digital representation of a spectrum via a Fourier transform infrared spectroscopy technique to calculate the quantity of at least one analyte for the spectrum, the system comprising:

means for performing the automated quantitative analysis, the analysis comprising an interferent correction technique;

means for specifying values to control the automated quantitative analysis, wherein the values to control the automated quantitative analysis comprise an indicator whether a suspect analysis condition should be monitored;

means for specifying values to detect possible aberrations in the automated quantitative analysis; and means for indicating possible aberrations in the automated quantitative analysis have been detected.

43. The system of claim 42 wherein the means for performing the automated quantitative analysis comprises computer-executable instructions for carrying out a Fourier transform infrared spectroscopy technique.

44. The automated system of claim 42 wherein the values to control the automated quantitative analysis further comprise a data output indicator.

45. The automated system of claim 42 wherein the values to control the automated quantitative analysis further comprise a parameter related to a negative peak area test.

46. The automated system of claim 42 wherein the values to control the automated quantitative analysis further comprise values for a signal-to-noise ratio test.

* * * * *

UNITED STATES PATENT AND TRADEMARK OFFICE
CERTIFICATE OF CORRECTION

| | | |
|---|---|---|
| PATENT NO. | : 7,206,701 B2 | |
| APPLICATION NO. | : 10/499443 | |
| DATED | : April 17, 2007 | |
| INVENTOR(S) | : Tuchman et al. | |

It is certified that error appears in the above-identified patent and that said Letters Patent is hereby corrected as shown below:

Col. 1, line 7      Delete the word "application"

Col. 16, line 33      "WIN IR" should be --WIN_IR--

Col. 16, line 62      "WIN IR" should be --WIN_IR--

Col. 22, line 41      "10 40,000" should be --10-40,000--

Col. 22, line 43      "UN-vis" should be --UV-vis--

Signed and Sealed this

Twenty-ninth Day of April, 2008

JON W. DUDAS
*Director of the United States Patent and Trademark Office*